United States Patent
Vendely et al.

(10) Patent No.: US 10,639,039 B2
(45) Date of Patent: May 5, 2020

(54) SURGICAL STAPLER BUTTRESS APPLICATOR WITH MULTI-ZONE PLATFORM FOR PRESSURE FOCUSED RELEASE

(71) Applicant: Ethicon Endo-Surgery, LLC, Guaynabo, PR (US)

(72) Inventors: Michael J. Vendely, Lebanon, OH (US); Trevor J. Barton, Cincinnati, OH (US); Jason L Harris, Lebanon, OH (US); Charles J. Scheib, Loveland, OH (US); Emily A. Schellin, Cincinnati, OH (US); Prudence A. Turner, Independence, KY (US)

(73) Assignee: Ethicon LLC, Guaynabo, PR (US)

( * ) Notice: Subject to any disclaimer, the term of this patent is extended or adjusted under 35 U.S.C. 154(b) by 816 days.

(21) Appl. No.: 14/926,296

(22) Filed: Oct. 29, 2015

(65) Prior Publication Data

US 2017/0056017 A1    Mar. 2, 2017

Related U.S. Application Data

(60) Provisional application No. 62/209,041, filed on Aug. 24, 2015.

(51) Int. Cl.
*A61B 17/10* (2006.01)
*A61B 17/072* (2006.01)
(Continued)

(52) U.S. Cl.
CPC ........ *A61B 17/07292* (2013.01); *A61B 50/30* (2016.02); *A61B 2017/0053* (2013.01);
(Continued)

(58) Field of Classification Search
CPC ........ A61B 17/07207; A61B 17/07292; A61B 2017/00004; A61B 2050/0059;
(Continued)

(56) References Cited

U.S. PATENT DOCUMENTS

| | | |
|---|---|---|
| 4,805,823 A | 2/1989 | Rothfuss |
| 5,415,334 A | 5/1995 | Williamson et al. |

(Continued)

FOREIGN PATENT DOCUMENTS

| | | |
|---|---|---|
| CN | 104 379 068 A | 2/2015 |
| EP | 2 090 248 A2 | 8/2009 |

(Continued)

OTHER PUBLICATIONS

European Search Report and Written Opinion dated Jan. 30, 2017 for Application No. EP 16185376.7, 14 pgs.

(Continued)

*Primary Examiner* — Paul R Durand
*Assistant Examiner* — Robert K Nichols, II
(74) *Attorney, Agent, or Firm* — Frost Brown Todd LLC

(57) ABSTRACT

An apparatus includes a housing, a platform, and a buttress assembly. The housing defines a gap configured to receive a portion of an end effector of a surgical stapler. A portion of the platform is exposed in the gap defined by the housing. The buttress assembly is positioned on the platform. The buttress assembly is exposed in the gap defined by the housing. The platform is configured to apply at least two different amounts of pressure against the first buttress assembly in response to a clamping action of an end effector positioned in the gap defined by the housing.

20 Claims, 21 Drawing Sheets

(51) Int. Cl.
*A61B 50/30* (2016.01)
*A61B 17/00* (2006.01)
*A61B 90/00* (2016.01)
*A61B 50/00* (2016.01)

(52) U.S. Cl.
CPC ............... *A61B 2017/00477* (2013.01); *A61B 2017/00862* (2013.01); *A61B 2017/00951* (2013.01); *A61B 2017/07221* (2013.01); *A61B 2017/07257* (2013.01); *A61B 2017/07271* (2013.01); *A61B 2050/0059* (2016.02); *A61B 2090/037* (2016.02)

(58) Field of Classification Search
CPC .... A61B 2090/037; A61B 2017/00477; A61B 2017/0053; A61B 2017/00862; A61B 2017/00951; A61B 2017/07221; A61B 2017/07257; A61B 2017/07271; A61B 17/072
See application file for complete search history.

(56) References Cited

U.S. PATENT DOCUMENTS

| | | | |
|---|---|---|---|
| 5,441,191 A | 8/1995 | Linden | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,752,965 A * | 5/1998 | Francis | A61B 17/07207 227/178.1 |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,273,897 B1 * | 8/2001 | Dalessandro | A61B 17/07207 606/139 |
| 6,364,888 B1 | 4/2002 | Niemeyer et al. | |
| 6,783,524 B2 | 8/2004 | Anderson et al. | |
| 6,939,358 B2 | 9/2005 | Palacios et al. | |
| 6,978,921 B2 | 12/2005 | Shelton, IV et al. | |
| 6,988,649 B2 | 1/2006 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney | |
| 7,691,098 B2 | 4/2010 | Wallace | |
| 7,721,930 B2 | 5/2010 | McKenna et al. | |
| 7,806,891 B2 | 10/2010 | Nowlin et al. | |
| 8,141,762 B2 | 3/2012 | Bedi et al. | |
| 8,210,032 B2 | 7/2012 | Sanford et al. | |
| 8,210,411 B2 | 7/2012 | Yates et al. | |
| 8,371,491 B2 | 2/2013 | Huitema et al. | |
| 8,408,439 B2 | 4/2013 | Huang et al. | |
| 8,453,904 B2 | 6/2013 | Eskaros et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,801,735 B2 | 8/2014 | Shelton, IV et al. | |
| 8,814,025 B2 | 8/2014 | Miller et al. | |
| 8,820,605 B2 | 9/2014 | Shelton, IV | |
| 8,844,789 B2 | 9/2014 | Shelton, IV et al. | |
| 8,899,464 B2 | 12/2014 | Hueil et al. | |
| 8,998,060 B2 | 4/2015 | Bruewer et al. | |
| 9,060,770 B2 | 6/2015 | Shelton, IV et al. | |
| 9,101,359 B2 | 8/2015 | Smith et al. | |
| 9,186,142 B2 | 11/2015 | Fanelli et al. | |
| 9,198,644 B2 | 12/2015 | Balek et al. | |
| 9,198,662 B2 | 12/2015 | Barton et al. | |
| 9,211,120 B2 | 12/2015 | Scheib et al. | |
| 9,220,501 B2 | 12/2015 | Baxter, III et al. | |
| 9,282,962 B2 | 3/2016 | Schmid et al. | |
| 9,300,773 B2 | 3/2016 | Mittleman et al. | |
| 9,301,759 B2 | 4/2016 | Spivey et al. | |
| 9,307,965 B2 | 4/2016 | Ming et al. | |
| 9,364,233 B2 | 6/2016 | Alexander, III et al. | |
| 9,393,018 B2 | 7/2016 | Wang et al. | |
| 9,398,911 B2 | 7/2016 | Auld | |
| 9,445,808 B2 * | 9/2016 | Woodard, Jr. | A61B 17/0401 |
| 9,492,170 B2 | 11/2016 | Bear et al. | |
| 9,517,065 B2 | 12/2016 | Simms et al. | |
| 9,770,245 B2 | 9/2017 | Swayze et al. | |
| 10,166,023 B2 | 1/2019 | Vendely et al. | |
| 10,342,532 B2 | 7/2019 | Zeiner et al. | |
| 10,345,542 B2 | 7/2019 | Rockman et al. | |
| 10,349,940 B2 | 7/2019 | Zeiner et al. | |
| 2003/0120284 A1 * | 6/2003 | Palacios | A61B 17/07207 606/139 |
| 2005/0070929 A1 * | 3/2005 | Dalessandro | A61B 17/07207 606/151 |
| 2006/0173470 A1 | 8/2006 | Oray et al. | |
| 2008/0169328 A1 | 7/2008 | Shelton, IV | |
| 2009/0206126 A1 | 8/2009 | Huitema et al. | |
| 2009/0206131 A1 | 8/2009 | Weisenburgh, II et al. | |
| 2009/0206142 A1 | 8/2009 | Huitema et al. | |
| 2010/0234861 A1 | 9/2010 | Oray et al. | |
| 2011/0290856 A1 | 12/2011 | Shelton, IV et al. | |
| 2012/0241492 A1 | 9/2012 | Shelton, IV et al. | |
| 2012/0241493 A1 | 9/2012 | Baxter, III et al. | |
| 2012/0289979 A1 | 11/2012 | Eskaros et al. | |
| 2012/0292367 A1 | 11/2012 | Morgan et al. | |
| 2013/0062391 A1 | 3/2013 | Boudreaux et al. | |
| 2013/0068816 A1 | 3/2013 | Vasudevan et al. | |
| 2013/0075447 A1 | 3/2013 | Weisenburgh, II et al. | |
| 2013/0206813 A1 | 8/2013 | Nalagatla | |
| 2013/0214030 A1 | 8/2013 | Aronhalt et al. | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239043 A1 | 8/2014 | Simms et al. | |
| 2014/0239044 A1 | 8/2014 | Hoffman | |
| 2014/0263563 A1 | 9/2014 | Stokes et al. | |
| 2015/0142023 A1 * | 5/2015 | Tannhauser | A61B 17/08 606/151 |
| 2015/0272575 A1 | 10/2015 | Leimbach et al. | |
| 2015/0351754 A1 | 12/2015 | Harris et al. | |
| 2015/0351758 A1 | 12/2015 | Shelton, IV et al. | |
| 2015/0351763 A1 | 12/2015 | Shelton, IV et al. | |
| 2015/0374360 A1 | 12/2015 | Scheib et al. | |
| 2015/0374373 A1 | 12/2015 | Rector et al. | |
| 2016/0089142 A1 | 3/2016 | Harris et al. | |
| 2016/0089146 A1 | 3/2016 | Harris et al. | |
| 2016/0278774 A1 * | 9/2016 | Shelton, IV | A61B 17/068 |
| 2017/0027567 A1 | 2/2017 | Scheib et al. | |
| 2017/0027568 A1 | 2/2017 | Scheib et al. | |
| 2017/0027569 A1 | 2/2017 | Scheib et al. | |
| 2017/0049444 A1 | 2/2017 | Schellin et al. | |
| 2017/0055980 A1 | 3/2017 | Vendely et al. | |
| 2017/0055981 A1 | 3/2017 | Vendely et al. | |
| 2017/0055982 A1 | 3/2017 | Zeiner et al. | |
| 2017/0055986 A1 | 3/2017 | Harris et al. | |
| 2017/0056016 A1 | 3/2017 | Barton et al. | |
| 2017/0056018 A1 | 3/2017 | Zeiner et al. | |

FOREIGN PATENT DOCUMENTS

| | | |
|---|---|---|
| EP | 2 764 833 A2 | 8/2014 |
| EP | 3 072 457 A2 | 9/2016 |

(56) References Cited

FOREIGN PATENT DOCUMENTS

| EP | 3072460 A2 | 9/2016 |
|---|---|---|
| WO | WO 2005/079675 A2 | 9/2005 |
| WO | WO 2013/119365 A1 | 8/2013 |

OTHER PUBLICATIONS

European Search Report and Written Opinion dated Jan. 24, 2017 for Application No. EP 16185387.4, 10 pgs.
International Search Report and Written Opinion dated Dec. 23, 2016 for Application No. PCT/US2016/048352, 16 pgs.
International Search Report and Written Opinion dated Feb. 17, 2017 for Application No. PCT/US2016/048356, 17 pgs.
International Search Report and Written Opinion dated Jan. 2, 2017 for Application No. PCT/US2016/048359, 12 pgs.
International Search Report and Written Opinion dated Dec. 21, 2016 for Application No. PCT/US2016/048362, 11 pgs.
International Search Report and Written Opinion dated Dec. 6, 2016 for Application No. PCT/US2016/048364, 12 pgs.
U.S. Appl. No. 14/871,071, filed Sep. 30, 2015.
U.S. Appl. No. 14/871,131, filed Sep. 30, 2015.
U.S. Appl. No. 14/926,027, filed Oct. 29, 2015.
U.S. Appl. No. 14/926,029, filed Oct. 29, 2015.
U.S. Appl. No. 14/926,045, filed Oct. 29, 2015.
U.S. Appl. No. 14/926,057, filed Oct. 29, 2015.
U.S. Appl. No. 14/926,072, filed Oct. 29, 2015.
U.S. Appl. No. 14/926,090, filed Oct. 29, 2015.
U.S. Appl. No. 14/926,131, filed Oct. 29, 2015.
U.S. Appl. No. 14/926,160, filed Oct. 29, 2016.
U.S. Appl. No. 14/926,194, filed Oct. 29, 2015.
U.S. Appl. No. 62/209,041, filed Aug. 24, 2015.
Extended European Search Report and Written Opinion dated Jan. 20, 2017 for Application No. EP 16185368.4, 10 pgs.
Extended European Search Report and Written Opinion dated Jan. 24, 2017 for Application No. EP 16185370.0, 11 pgs.
Extended European Search Report and Written Opinion dated Jun. 8, 2017 for Application No. EP 16185375.9, 16 pgs.
European Search Report, Extended, and Written Opinion dated Oct. 18, 2017 for Application No. EP 18182626.4, 8 pgs.
European Exam Report dated Oct. 16, 2018 for Application No. EP 16185368.4, 4 pgs.
U.S. Appl. No. 14/926,764.
European Examination Report dated Jan. 3, 2018 for Application No. EP 16185368.4, 4 pgs.
European Examination Report dated Jan. 15, 2018 for Application No. EP 16185370.0, 4 pgs.
U.S. Appl. No. 14/926,267.
U.S. Appl. No. 14/926,358.
U.S. Appl. No. 14/926,609.
U.S. Appl. No. 14/926,322.
U.S. Appl. No. 16/191,722.
U.S. Appl. No. 16/211,436.
U.S. Appl. No. 16/211,438.
U.S. Appl. No. 16/377,348.
European Communication, Decision to Grant a European Patent, dated Jan. 10, 2019 for Application No. EP 16185376.7, 2 pgs.
European Search Report, Partial, dated Jan. 25, 2017 for Application No. 16185375.9, 7 pgs.
European Communication, Decision to Grant a European Patent, dated Dec. 6, 2018 for Application No. EP 16185375.9, 2 pgs.
European Communication, Decision to Grant a European Patent, dated Jul. 4, 2019 for Application No. EP 16185370.0, 2 pgs.
European Communication, Decision to Grant a European Patent, dated Aug. 30, 2018 for Applicafion No. EP 16185387.4, 2 pgs.

* cited by examiner

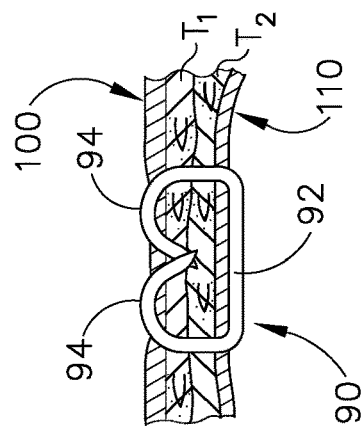
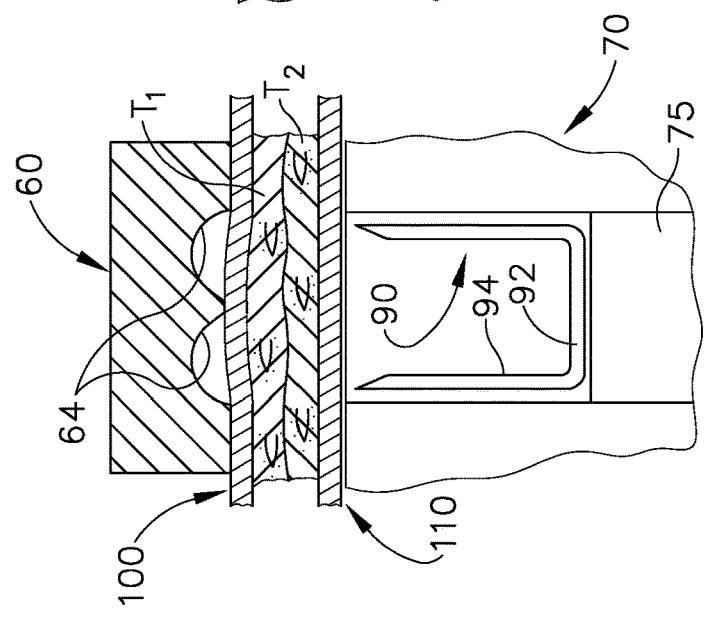
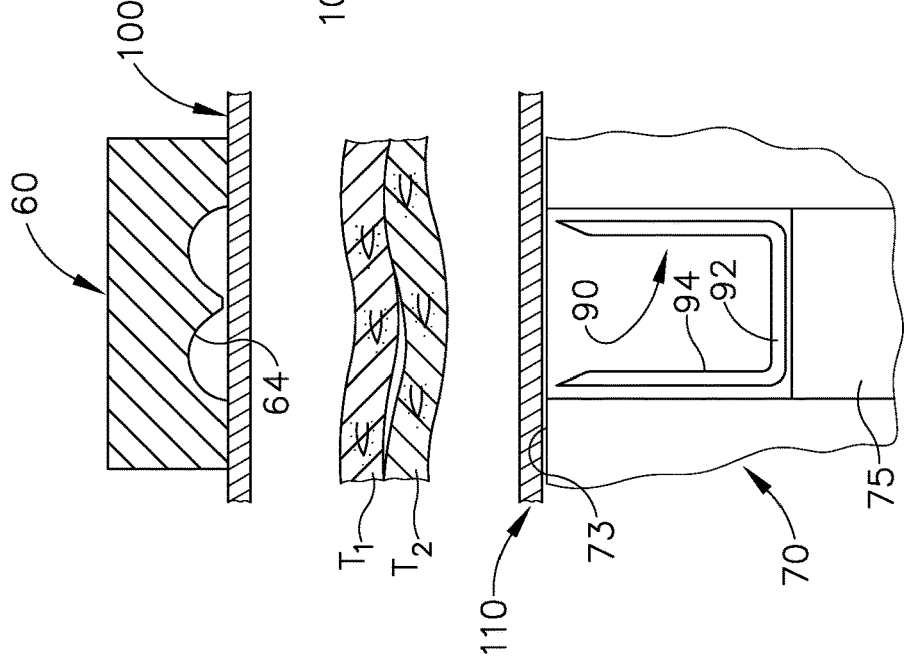

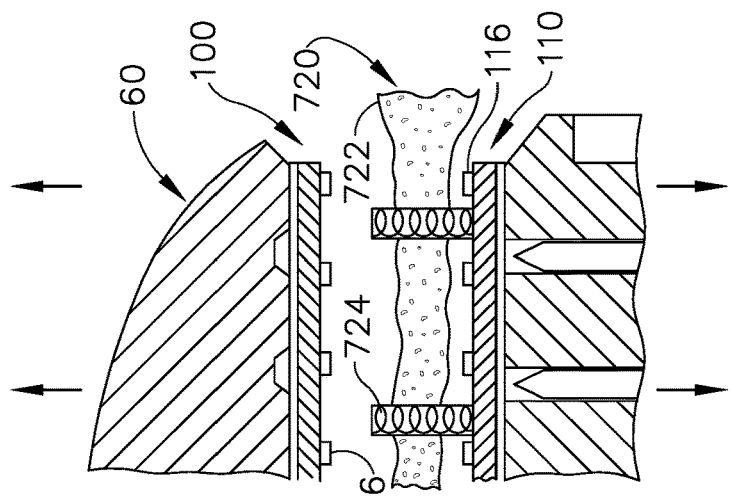
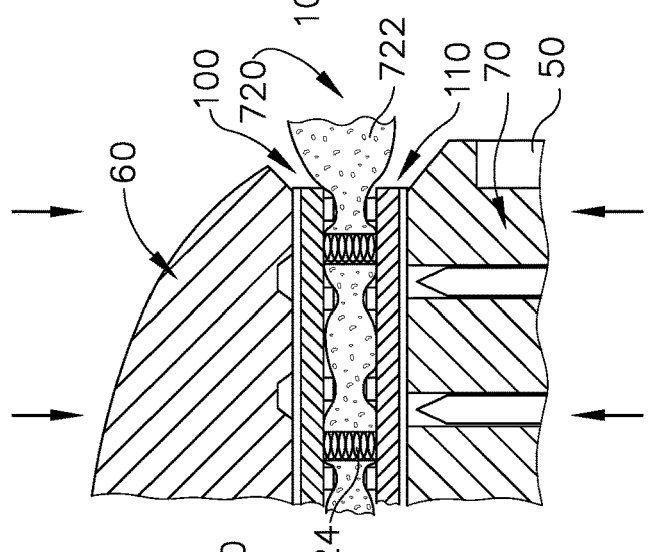
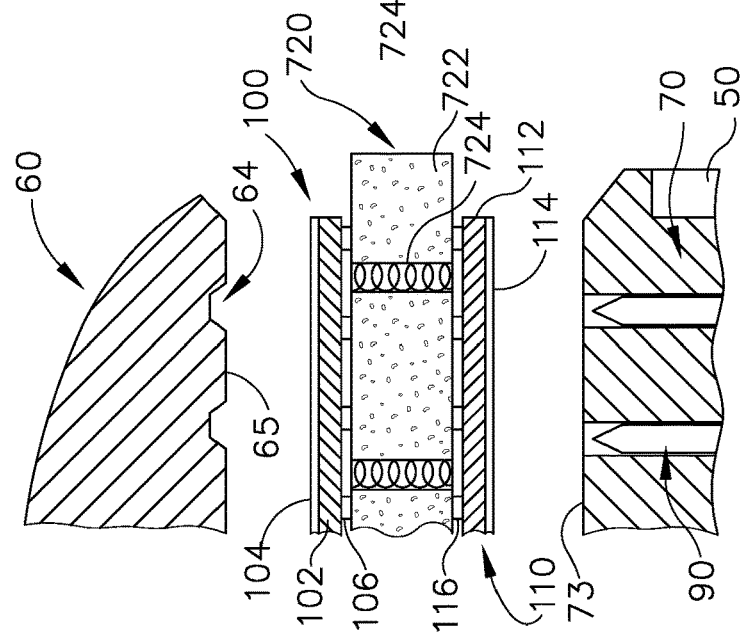

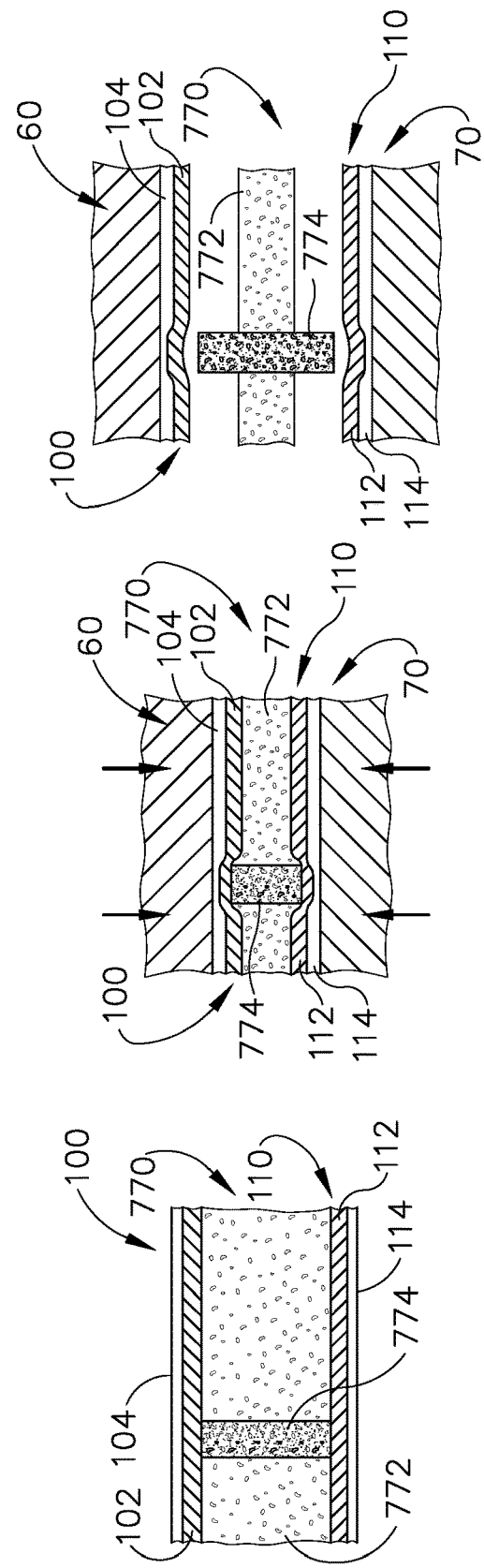

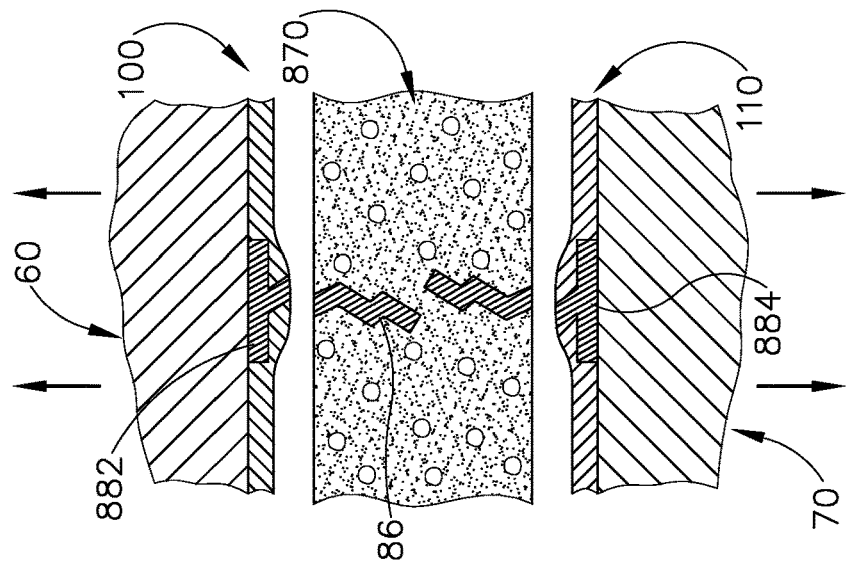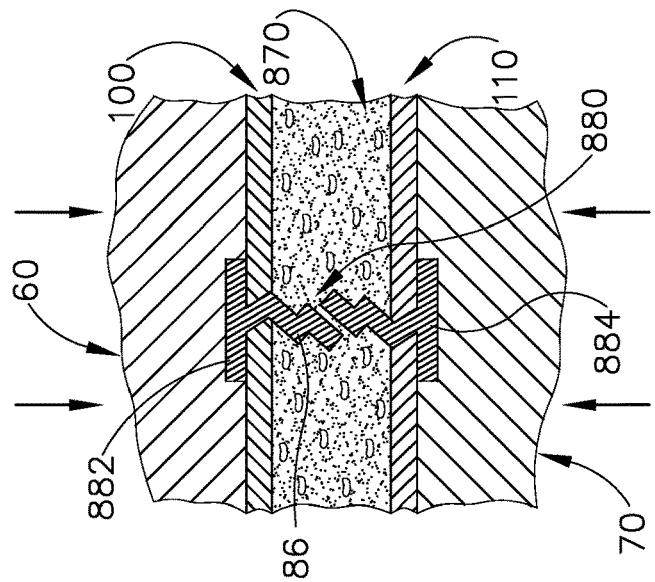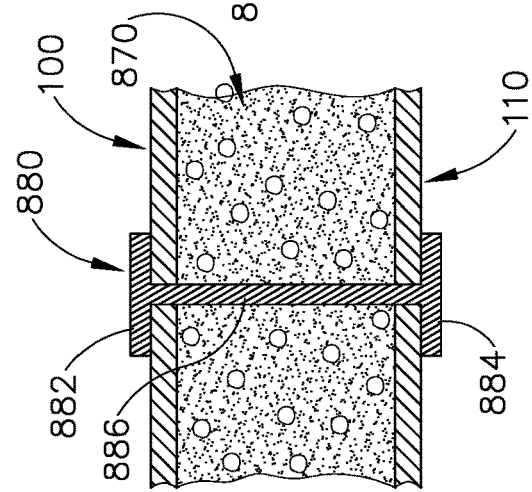

SURGICAL STAPLER BUTTRESS APPLICATOR WITH MULTI-ZONE PLATFORM FOR PRESSURE FOCUSED RELEASE

PRIORITY

This application claims priority to U.S. Patent App. No. 62/209,041, entitled "Method and Apparatus for Applying a Buttress to End Effector of a Surgical Stapler," filed Aug. 24, 2015, the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2018; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, issued as U.S. Pat. No. 9,597,082 on Mar. 21, 2017; U.S. Pub. No. 2014/0246473, entitled "Rotary Powered Surgical Instruments with Multiple Degrees of Freedom," published Sep. 4, 2014, issued as U.S. Pat. No. 9,398,911 on Jul. 26, 2016; U.S. Pub. No. 2013/0206813, entitled "Linear Stapler," published Aug. 15, 2013, now abandoned; U.S. Pub. No. 2008/0169328, entitled "Buttress Material for Use with a Surgical Stapler," published Jul. 17, 2008, now abandoned; U.S. patent application Ser. No. 14/300,804, entitled "Woven and Fibrous Materials for Reinforcing a Staple Line," filed Jun. 10, 2014, issued as U.S. Pat. No. 9,848,871 on Dec. 26, 2017; U.S. patent application Ser. No. 14/300,811, entitled "Devices and Methods for Sealing Staples in Tissue", issued as U.S. Pat. No. 9,936,954 on Apr. 10, 2018; and U.S. patent application Ser. No. 14/498,070, entitled "Circular Fastener Cartridges for Applying Radially Expandable Fastener Lines" filed Sep. 26, 2014, issued as U.S. Pat. No. 10,426,476 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 5A depicts a cross-sectional end view of a portion of the end effector of FIG. 2 with a buttress assembly formed by the buttresses of FIG. 4 applied to the end effector, with tissue positioned between the buttresses in the end effector, and with the anvil in an open position;

FIG. 5B depicts a cross-sectional end view of the combined end effector and buttress assembly of FIG. 5A, with tissue positioned between the buttresses in the end effector, and with the anvil in a closed position;

FIG. 5C depicts a cross-sectional view of a staple and the buttress assembly of FIG. 5A having been secured to the tissue by the end effector of FIG. 2;

FIG. 14A depicts a partial, cross-sectional end view of a buttress assembly disposed on a platform of the buttress applier cartridge of FIG. 13, with the buttress assembly and platform positioned in the end effector of FIG. 2, and with the end effector in an open configuration;

FIG. 14B depicts a partial, cross-sectional end view of the buttress assembly and platform of FIG. 14A, with the end effector in a closed configuration;

FIG. 14C depicts a partial, cross-sectional end view of the buttress assembly and anvil of FIG. 14A, with the end effector in an open configuration, and with an upper portion of the buttress assembly adhered to the anvil and a lower portion of the buttress assembly adhered to the deck of the staple cartridge;

FIG. 15A depicts a partial, cross-sectional end view of a buttress assembly disposed on an exemplary variation of the platform of FIG. 14A;

FIG. 15B depicts a partial, cross-sectional end view of the buttress assembly and platform of FIG. 15A, with the buttress assembly and platform positioned in the end effector of FIG. 2, and with the end effector in a closed configuration;

FIG. 15C depicts a partial, cross-sectional end view of the buttress assembly and anvil of FIG. 15A, with the end effector in an open configuration, and with an upper portion of the buttress assembly adhered to the anvil and a lower portion of the buttress assembly adhered to the deck of the staple cartridge;

FIG. 22A depicts a partial, cross-sectional end view of a platform and buttress assembly of another exemplary alternative buttress applier cartridge, with a retention post assembly in an intact state;

FIG. 22B depicts a partial, cross-sectional end view of the platform and buttress assembly of FIG. 22A, with the end effector of FIG. 2 compressing the platform and buttress assembly, thereby transitioning the retention post assembly to a fractured state;

FIG. 22C depicts a partial, cross-sectional end view of the platform and buttress assembly of FIG. 22A, with the end effector in an open configuration, with the buttress assembly adhered to the end effector, and with a portion of the retention post assembly remaining in a fractured state in the platform;

Figure 1:
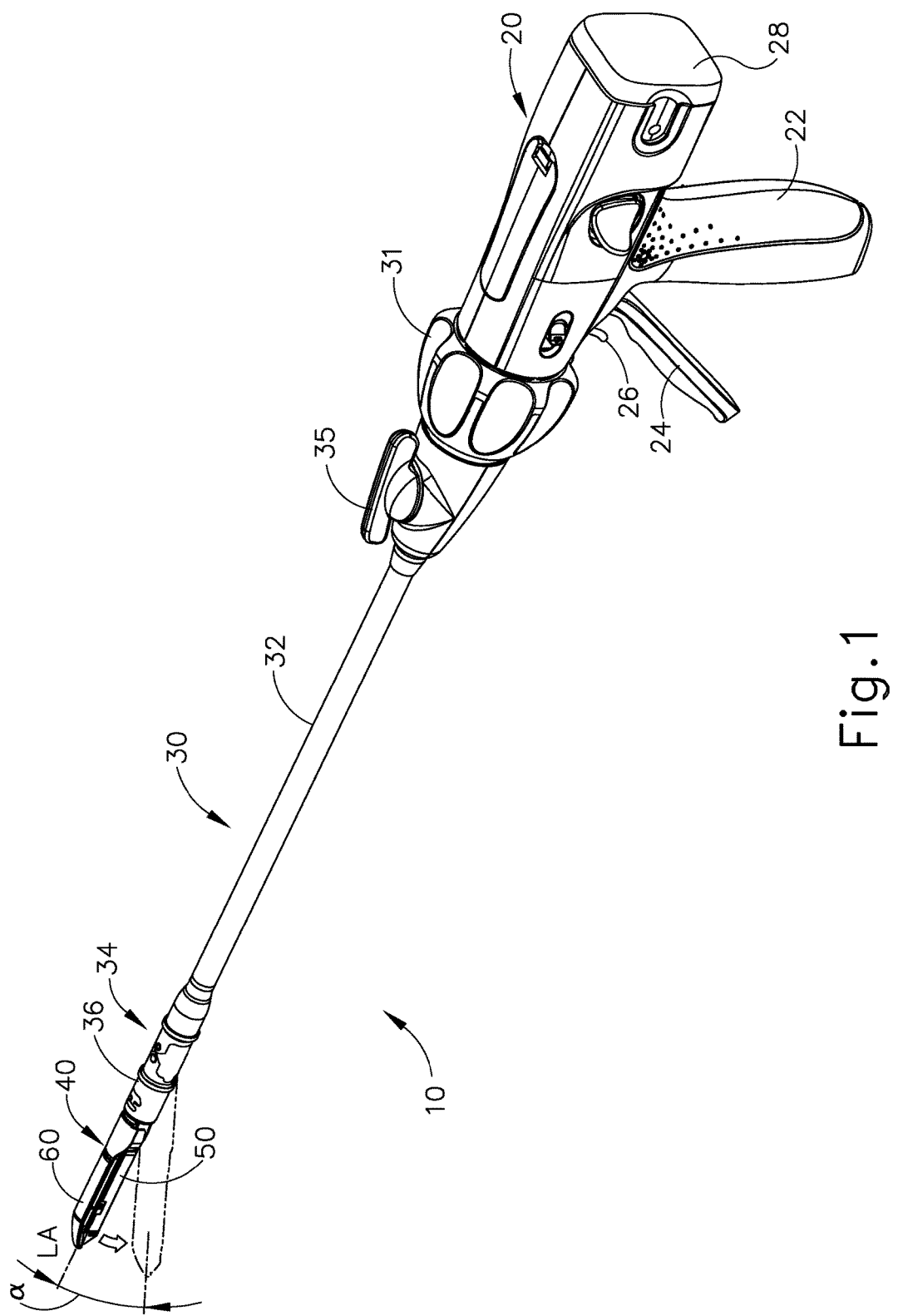
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY SURGICAL STAPLER

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
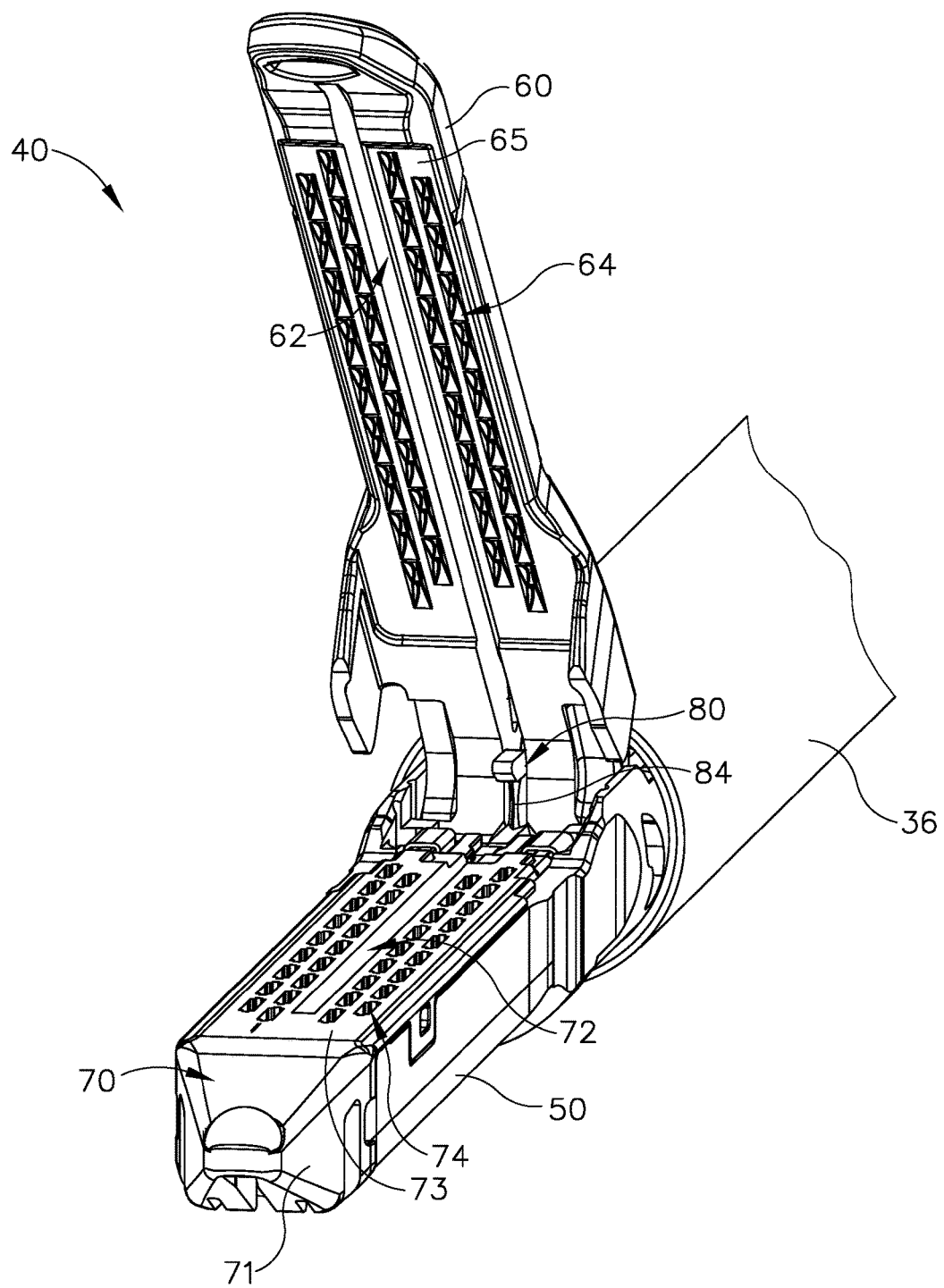
FIG. 2 depicts a perspective view of an end effector of the instrument of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein; and/or U.S. patent application Ser. No. 14/314,125, entitled "Articulation Drive Features for Surgical Stapler," filed Jun. 25, 2014, issued as U.S. Pat. No. 10,292,701 on May 21, 2019, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
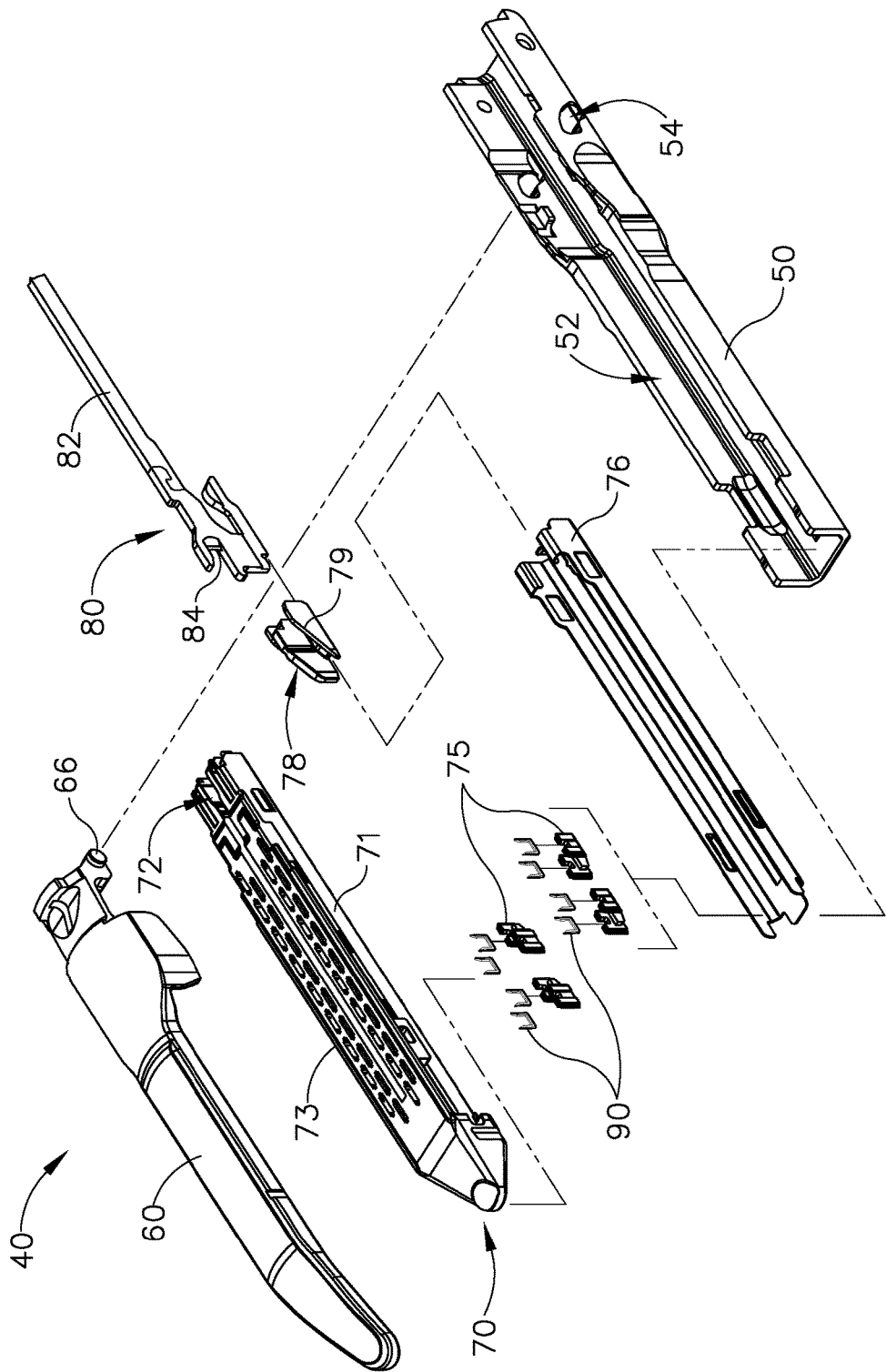
FIG. 3 depicts an exploded perspective view of the end effector of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Method of Using Lockout Features for Surgical Stapler Cartridge," filed on Jun. 25, 2014, issued as U.S. Pat. No. 10,335,147 on Jul. 2, 2019, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. EXEMPLARY BUTTRESS ASSEMBLY FOR SURGICAL STAPLER

In some instances, it may be desirable to equip end effector (40) with a buttress material to reinforce the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress Assembly for Surgical Stapler

Figure 4:
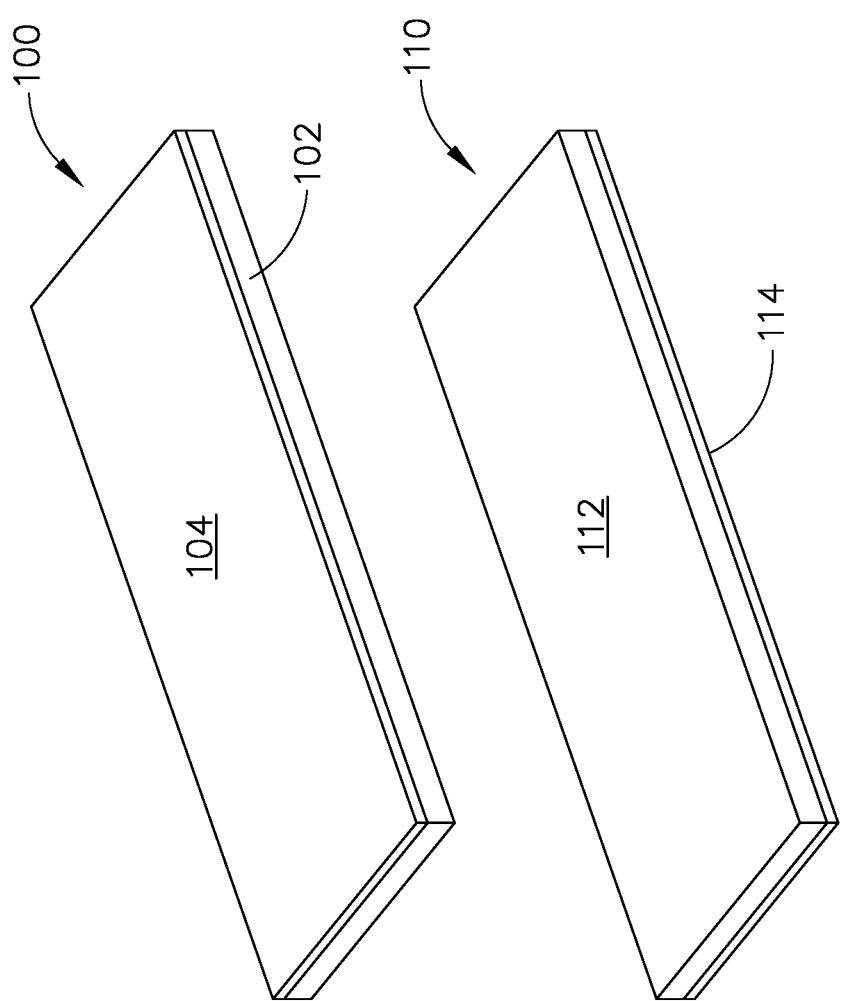
FIG. 4 depicts a perspective view of an exemplary upper buttress and an exemplary lower buttress, each of which may be applied to the end effector of FIG. 2.

FIG. 4 shows an exemplary pair of buttress assemblies (100, 110) with a basic composition. Buttress assembly (100) of this example comprises a buttress body (102) and an upper adhesive layer (104). Similarly, buttress assembly (110) comprises a buttress body (112) and a lower adhesive layer (114). In the present example, each buttress body (102, 112) comprises a strong yet flexible material configured to structurally support a line of staples (90). By way of example only, each buttress body (102, 112) may comprise a woven mesh of polyglactin 910 material by Ethicon, Inc. of Somerville, N.J. Alternatively, any other suitable materials or combinations of materials may be used in addition to or as an alternative to polyglactin 910 material to form each buttress body (102, 112). Each buttress body (102, 112) may take any other suitable form and may be constructed of any other suitable material(s). By way of further example only, each buttress body (102, 112) may comprise one or more of the following: NEOVEIL absorbable PGA felt by Gunze Limited, of Kyoto, Japan; SEAMGUARD polyglycolic acid:trimethylene carbonate (PGA:TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress body (102, 112) will be apparent to those of ordinary skill in the art in view of the teachings herein.

In addition or in the alternative, each buttress body (102, 112) may comprise a material including, for example, a hemostatic agent such as fibrin to assist in coagulating blood and reduce bleeding at the severed and/or stapled surgical site along tissue (90). As another merely illustrative example, each buttress body (102, 112) may comprise other adjuncts or hemostatic agents such as thrombin may be used such that each buttress body (102, 112) may assist to coagulate blood and reduce the amount of bleeding at the surgical site. Other adjuncts or reagents that may be incorporated into each buttress body (102, 112) may further include but are not limited to medical fluid or matrix components. Merely illustrative examples of materials that may be used to form each buttress body (102, 112), as well as materials that may be otherwise incorporated into each buttress body (102, 112), are disclosed in U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein. Alternatively, any other suitable materials may be used.

By way of further example only, each buttress body (102, 112) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid Fillable Buttress," published Mar. 14, 2013, issued as U.S. Pat. No. 9,999,408 on Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814,025 on Aug. 26, 2014, the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,899,464 on Dec. 2, 2014, the disclosure of which is incorporated by reference herein; U.S. Patent Pub. No. 2013/0037596, entitled "Device for Applying Adjunct in Endoscopic Procedure," published Feb. 14, 2013, issued as U.S. Pat. No. 9,492,170 on Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, issued as U.S. Pat. No. 8,998,060 on Apr. 7, 2015, the disclosure of which is incorporated by reference herein; U.S. Patent Pub. No. 2013/0075446, entitled "Surgical Staple Assembly with Hemostatic Feature," published Mar. 28, 2013, issued as U.S. Pat. No. 9,393,018 on Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No. 2013/0075445, entitled "Anvil Cartridge for Surgical Fastening Device," published Mar. 28, 2013, issued as U.S. Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; U.S. Patent Pub. No. 2013/0256367, entitled "Tissue Thickness Compensator Comprising a Plurality of Medicaments," published Oct. 3, 2013, issued as U.S. Pat. No. 9,211,120 on Dec. 15, 2015, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, issued as U.S. Pat. No. 10,172,611 on Jan. 8, 2019, the disclosure of which is incorporated by reference herein; U.S. patent application Ser. No. 14/827,856, entitled "Implantable Layers for a Surgical Instrument," filed Aug. 17, 2015, published as U.S. Pub. No. 2017/0049444 on Feb. 23, 2017, the disclosure of which is incorporated by reference herein; U.S. patent application Ser. No. 14/840,613, entitled "Medical Eluting Adjuncts and Methods of Using Medicant Eluting Adjuncts," filed Aug. 31, 2015, published as U.S. Pub. No. 2017/00055986 on Mar. 2, 2017, the disclosure of which is incorporated by reference herein; U.S. patent application Ser. No. 14/871, 071, entitled "Compressible Adjunct with Crossing Spacer Fibers," filed Sep. 30, 2015, issued as U.S. Pat. No. 10,433, 846 on Oct. 8, 2019, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30,2017, the disclosure of which is incorporated by reference herein.

In the present example, adhesive layer (104) is provided on buttress body (102) in order to adhere buttress body (102) to underside (65) of anvil (60). Similarly, adhesive layer (114) is provided on buttress body (112) in order to adhere buttress body (112) to deck (73) of staple cartridge (70). Adherence of the buttress body (102) to underside (65) of anvil (60) or to deck (73) of staple cartridge (70) can occur through a variety of mechanisms including but not limited to a pressure sensitive adhesive. In some versions, each adhesive layer (104, 114) comprise a pressure sensitive adhesive material. Examples of various suitable materials that may be used to form adhesive layers (104, 114) are disclosed in U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein. Alternatively, any other suitable materials may be used. It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (104, 114) will be apparent to those of ordinary skill in the art in view of the teachings herein.

B. Exemplary Materials and Techniques for Providing Adhesion of Buttress to Surgical Stapler As noted above, a buttress assembly (100, 110) may include a layer (104, 114) of adhesive material (or other form of adhesive material) that adheres buttress body (102, 112) to either underside (65) of anvil (60) or deck (73) of staple cartridge (70). Such an adhesive material may provide proper positioning of buttress body (102, 112) before and during actuation of end effector (40); then allow buttress body (102, 112) to separate from end effector (40) after end effector (40) has been actuated, without causing damage to buttress body (102, 112) that is substantial enough to compromise the proper subsequent functioning of buttress body (102, 112).

FIGS. 5A-5C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 5A shows layers of tissue ($T_1$, $T_2$) positioned between anvil (60) and staple cartridge (70), with anvil (60) in the open position. Buttress assembly (100) is adhered to the underside (65) of anvil (60) via adhesive layer (104); while buttress assembly (110) is adhered to deck (73) of staple cartridge (70) via adhesive layer (114). Layers of tissue ($T_1$, $T_2$) are thus interposed between buttress assemblies (100, 110). Next, trigger (24) is pivoted toward pistol grip (22) to drive closure tube (32) and closure ring (36) distally. This drives anvil (60) to the closed position as shown in FIG. 5B. At this stage, layers of tissue ($T_1$, $T_2$) are compressed between anvil (60) and staple cartridge (70), with buttress assemblies (100, 110) engaging opposite surfaces of tissue layers ($T_1$, $T_2$). End effector (40) is then actuated as described above, driving staple (90) through buttress assemblies (100, 110) and tissue (90). As shown in FIG. 5C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 6:
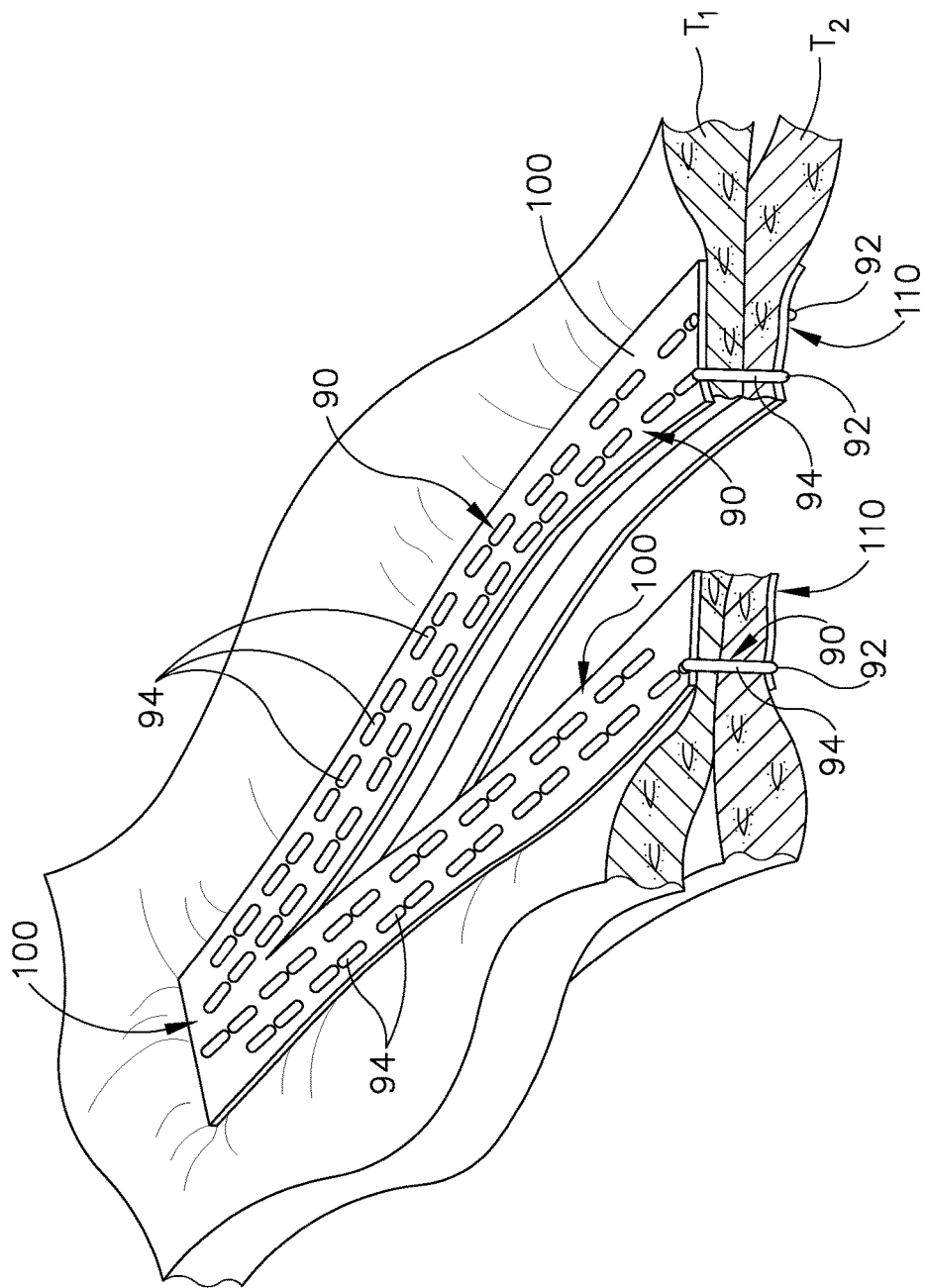
FIG. 6 depicts a perspective view of staples and the buttress assembly of FIG. 5A having been secured to the tissue by the end effector of FIG. 2.

It should be understood that a series of staples (90) will similarly capture and retain buttress assemblies (100, 110) against layers of tissue ($T_1$, $T_2$), thereby securing buttress assemblies (100, 110) to tissue ($T_1$, $T_2$) as shown in FIG. 6. As end effector (40) is pulled away from tissue (90) after deploying staples (90) and buttress assemblies (100, 110), buttress assemblies (100, 110) disengage end effector), such that buttress assemblies (100, 110) remain secured to tissue ($T_1$, $T_2$) with staples (90). Buttress tissue ($T_1$, $T_2$) thus provide structural reinforcement to the lines of staples (90). As can also be seen in FIG. 6, knife member (80) also cuts through a centerline of buttress tissue assemblies (100, 110), separating each buttress assemblies (100, 110) into a corresponding pair of sections, such that each section remains secured to a respective severed region of tissue ($T_1$, $T_2$).

In the foregoing example, buttress assembly (100) is sized to span across the full width of underside (65), such that buttress assembly (100) spans across channel (62). Thus, knife member (80) cuts through buttress assembly (100) during actuation of end effector (40) as described above. In some other examples, such as those described below, buttress assembly (100) is provided in two separate, laterally spaced apart portions, with one portion being disposed on underside (65) on one side of channel (62) and another portion being disposed on underside (65) on the other side of channel (62). In such versions, buttress assembly (100) does not span across channel (62), such that knife member (80) does not cut through buttress assembly (100) during actuation of end effector (40).

Likewise, buttress assembly (110) may be sized to span across the full width of deck (73), such that buttress assembly (110) spans across channel (72), and such that knife member (80) cuts through buttress assembly (110) during actuation of end effector (40) as described above. Alternatively, buttress assembly (110) may be provided in two separate, laterally spaced apart portions, with one portion being disposed on deck (73) on one side of channel (72) and another portion being disposed on deck (73) on the other side of channel (72), such that buttress assembly (110) does not span across channel (72), and such that knife member (80) does not cut through buttress assembly (110) during actuation of end effector (40).

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein.

III. EXEMPLARY BUTTRESS APPLIER CARTRIDGE

As noted above, buttress assembly (100) may be applied to the underside (65) of anvil (60), and buttress (110) may be applied to deck (73) of staple cartridge (70), before tissue (T₁, T₂) is positioned in end effector (40), and before end effector (40) is actuated. Because end effector (40) may be actuated many times during use of instrument (10) in a single surgical procedure, it may be desirable to enable an operator to repeatedly and easily load buttress assemblies (100) on underside (65) of anvil (60) during that single surgical procedure. In other words, because end effector (40) may be actuated many times during use of instrument (10) in a single surgical procedure, it may be insufficient to simply provide anvil (60) pre-loaded with a buttress assembly (100) without facilitating the re-loading of anvil (60) with additional buttress assemblies (100) after end effector (40) has been actuated.

Similarly, those of ordinary skill in the art will recognize that staple cartridge (70) will need to be replaced each time end effector (40) is actuated. When end effector (40) is actuated several times during use of instrument (10) in a single surgical procedure, several staple cartridges (70) may thus be used during that surgical procedure. It may seem that each of these staple cartridges (70) may be provided with buttress assembly (110) pre-loaded on deck (73). However, there are some reasons why it may be undesirable to provide a staple cartridge (70) with buttress assembly (110) pre-loaded on deck (73). In other words, it may be desirable to provide loading of buttress assembly (110) on deck (73) immediately prior to usage of staple cartridge in the surgical procedure, rather than loading buttress assembly (110) on deck (73) a substantial time prior to the surgical procedure. For instance, buttress assembly (110) may not be compatible with the same sterilization techniques as staple cartridge (70), such that it may present processing difficulties to package staple cartridge (70) with buttress assembly (110) pre-loaded on deck (73). In addition, the material forming buttress assembly (110) may have certain environmental sensitivities that staple cartridge (70) does not have, such that it may be beneficial to enable buttress assembly (110) and staple cartridge (70) to be stored separately before use. Moreover, buttress assembly (110) may not be warranted or otherwise desired in some surgical procedures, such that it may be desirable to enable a physician to easily choose whether staple cartridge (70) should be loaded with buttress assembly (110) before that staple cartridge (70) is used in the surgical procedure.

In view of the foregoing, it may be desirable to enable an operator to repeatedly and easily load buttress assemblies (100, 110) on end effector (40) on an ad hoc basis during a given surgical procedure. It may also be desirable to provide a device that provides support and protection to buttress assemblies (100, 110) before buttress assemblies (100, 110) are loaded on end effector (40), in addition to that same device also enabling buttress assemblies (100, 110) to be easily loaded on end effector. The examples described below relate to various cartridge assemblies that provide such support, protection, and loading of buttress assemblies (100, 110). It should be understood that the following examples are merely illustrative. Numerous variations will be apparent to those of ordinary skill in the art in view of the teachings herein.

Figure 7:
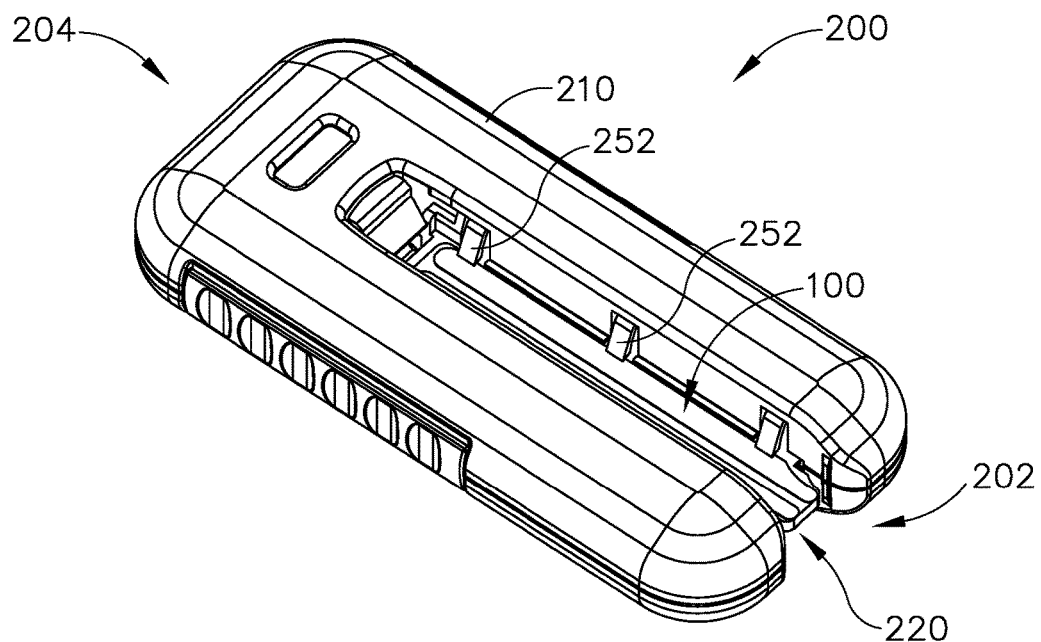
FIG. 7 depicts a perspective view of an exemplary buttress applier cartridge that may be used to carry and apply the buttress assembly of FIG. 5A.
Figure 8:
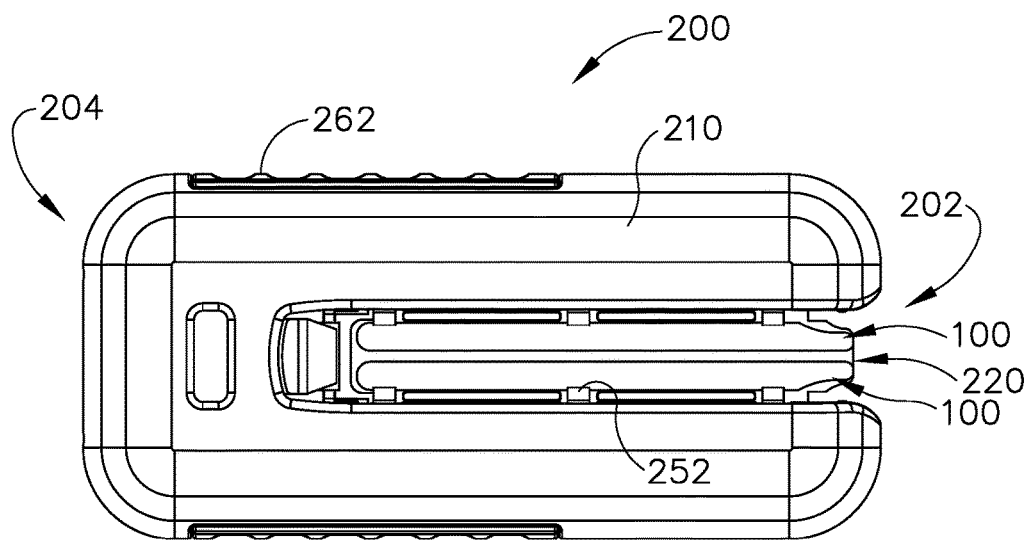
FIG. 8 depicts a top plan view of the buttress applier cartridge of FIG. 7.

FIGS. 7-9B show an exemplary buttress applier cartridge (200) that may be used to support and protect buttress assemblies (100, 110). Cartridge (200) may also be used to easily load buttress assemblies (100, 110) on end effector (40). As best seen in FIGS. 7-8, cartridge (200) of this example comprises an open end (202) and a closed end (204). Open end (202) is configured to receive end effector (40) as will be described in greater detail below. Cartridge (200) further includes a first housing (210) that generally defines a "U" shape to present open end (202). Cartridge (200) further includes a platform (220) and a set of retainers (252), Platform (220) of the present example is configured to support a pair of buttress assemblies (100) via retainer arms (252) on one side of platform (220) and another pair of buttress assemblies (110) on the other side of platform (220) via retainer arms (252). Platform (220) is exposed in recesses that are formed between the prongs of the "U" configuration of housing (210). The location of platform (220) and buttress assemblies (100, 110) in such recesses may prevent inadvertent contact between buttress assemblies (100, 110) and other devices in the operating room. In other words, housings (210, 218) may provide some degree of physical shielding of buttress assemblies (100, 110).

In the present example, each buttress assembly (100, 110) is provided in a respective pair of portions that are separated to avoid spanning across channels (62, 72) of anvil (60) and staple cartridge (70), respectively, though it should be understood that platform (220) may just as easily support wide versions of buttress assemblies (100, 110) that unitarily span across channels (62, 72) of anvil (60) and staple cartridge (70), respectively. The outer edges of platform (220) are captured within housing (210) and include retention features to prevent platform (220) from sliding relative to housing (210). In some versions, platform (220) is formed of a material that provides a high coefficient of friction, thereby reducing any tendency that buttress assemblies (100, 110) might otherwise have to slide along corresponding surfaces of platform (220). For instance, platform (220) may comprise an elastomeric material and/or a foam material. In some instances, platform (220) is formed of a compressible foam material that is configured to maintain a compressed configuration after being compressed by end effector (40). By way of example only, platform (220) may comprise Santoprene, closed-cell polyurethane foam, any other compressible material, and/or a material that may be made compressible via geometry (e.g., a rubber material with deformable standing features). Various suitable materials and structural configurations that may be used to form platform (220) will be apparent to those of ordinary skill in the art in view of the teachings herein.

Retainer arms (252) of the present example are configured to selectively secure buttress assemblies (100, 110) to platform (220). In particular, buttress assemblies (100, 110) are interposed between the free ends of arms (252) and platform (220). In the present example, retainer arms (252) are movable laterally outwardly such that retainer arms (252) disengage buttress assemblies (100, 110), thereby enabling buttress assemblies (100, 110) to be removed from platform (220). Retainer arms (252) are resilient and are thus configured to resiliently bear against buttress assemblies (100, 110), thereby pinching buttress assemblies (100, 110) against platform (220). Other suitable ways in which retainer arms (252) may engage buttress assemblies (100, 110) will be apparent to those of ordinary skill in the art in view of the teachings herein.

Figure 9A:
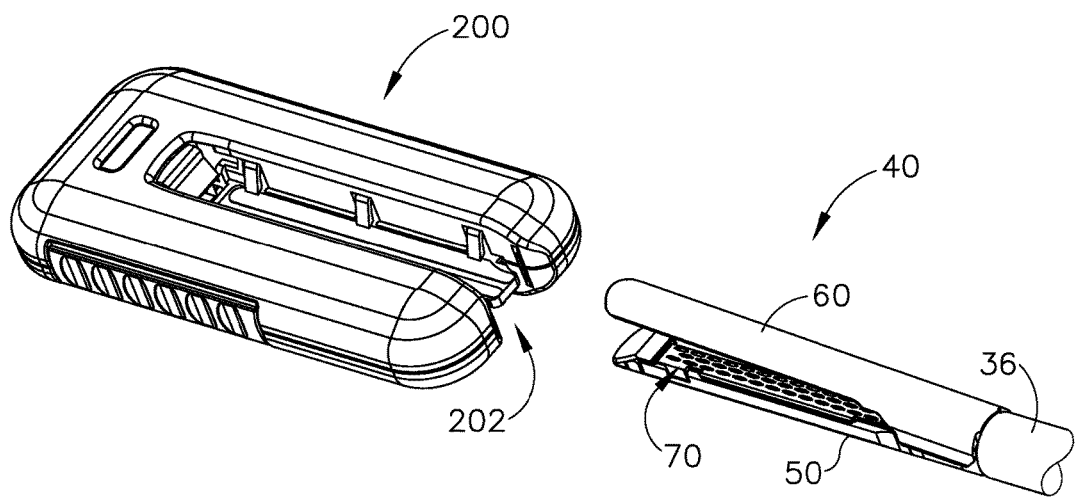
FIG. 9A depicts a perspective view of the end effector of FIG. 2 and the buttress applier cartridge of FIG. 7, with the end effector approaching the buttress applier cartridge.
Figure 9B:
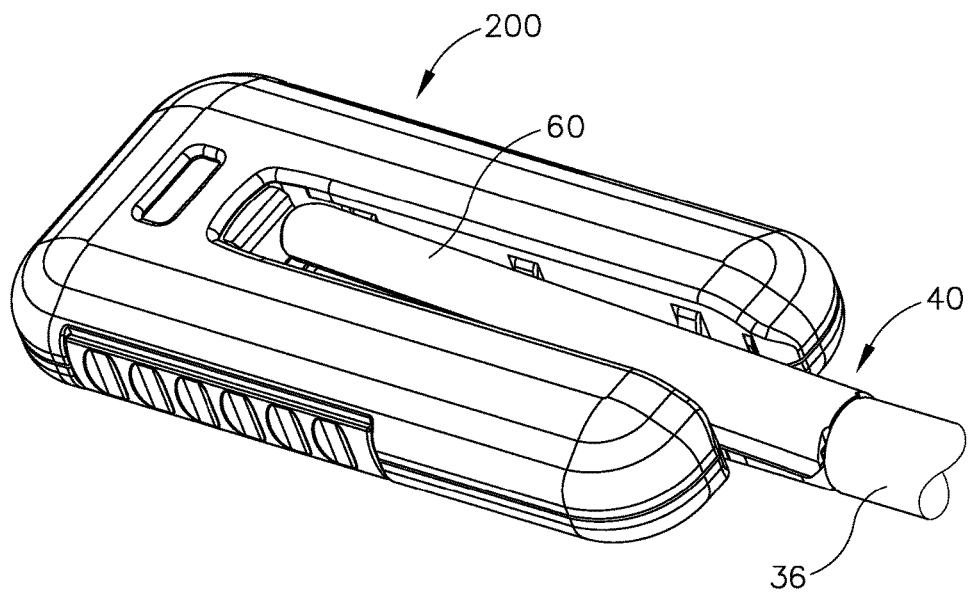
FIG. 9B depicts a perspective view of the end effector of FIG. 2 and the buttress applier cartridge of FIG. 7, with the buttress applier cartridge positioned in the end effector.

To use cartridge (200) to load end effector (40), the operator would first position cartridge (200) and end effector (40) such that end effector is aligned with open end (202) of cartridge (200) as shown in FIG. 9A. The operator would then advance end effector (40) distally (and/or retract cartridge (200) proximally) to position platform (220) and buttress assemblies (100, 110) between anvil (60) and staple cartridge (70) as shown in FIG. 9B. In order to load buttress assemblies (100, 110) on end effector (40), the operator may simply close end effector (40) by pivoting anvil (60) toward staple cartridge (70), as described above. Such closure of end effector (40) will result in disengagement of retainer arms (252) from buttress assemblies (100, 110). With end effector (40) clamping on both buttress assemblies (100, 110), adhesive layers (104, 114) are adhered to underside (65) of anvil (60) and deck (73) of staple cartridge (70). End effector (40) may then be re-opened (i.e., pivoting anvil (60) away from staple cartridge (70)) and pulled away from cartridge (200). With retainer arms (252) disengaged from buttress assemblies (100, 110), end effector (40) may freely pull buttress assemblies (100, 110) away from platform (220) as end effector (40) is pulled away from cartridge (200). With buttress assemblies (100, 110) loaded on end effector (40), end effector (40) may then be used as described above with reference to FIGS. 5A-6.

In addition to or in lieu of the foregoing, cartridge (200) may be constructed and operable in accordance with at least some of the teachings of U.S. Patent App. No. 62/209,041, entitled "Method and Apparatus for Applying a Buttress to End Effector of a Surgical Stapler," filed Aug. 25, 2015, the disclosure of which is incorporated by reference herein.

IV. EXEMPLARY BUTTRESS APPLIER CARTRIDGE WITH PLATFORM PROVIDING LOCALIZED PRESSURE

In the example above, platform (220) is provided as a generally flat, stationary members that simply provide support to buttress assemblies (100, 110) until buttress assemblies (100, 110) are adhered to end effector (40). It may be desirable to provide additional functionality to platform (220). For instance, it may be desirable to incorporate features into platform (220) that further promote adhesion of buttress assemblies (100, 110) to end effector (40). This may be done by providing variation of pressure among certain areas of end effector (40) when end effector (40) clamps down on buttress assemblies (100, 110) and platform (220). In particular, pressure may be localized or otherwise applied differently based on the location on platform (220) by providing surface features that concentrate compressive forces in certain regions of the entire clamping footprint of end effector (40). The concentration of compressive forces in these regions may provide greater adhesion in those regions than might otherwise be achieved through versions where platform (220) is simply flat. The following examples include several ways in which platform (220) may provide different amounts of pressure based on the location on the platform. It should be understood that any of the platforms described below may be readily incorporated into cartridge (200) as described above.

Figure 10:
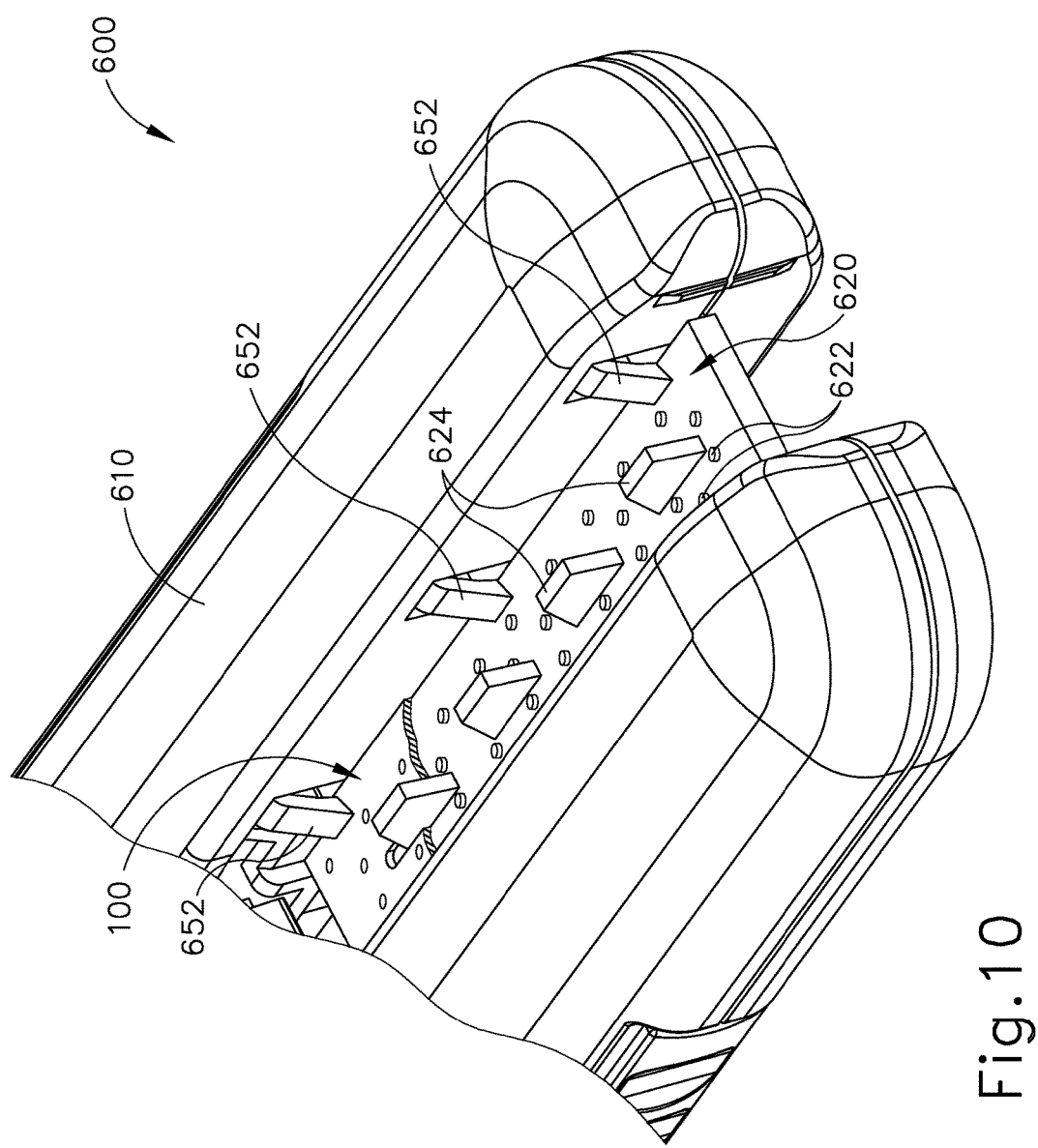
FIG. 10 depicts a partial perspective view of an open end of another exemplary buttress applier cartridge that may be used to carry and apply the buttress assembly of FIG. 5A.

A. Exemplary Buttress Applier Cartridge with Platform Having Localized Pressure Applying Surface Features FIG. 10 shows an exemplary alternative buttress applier cartridge (600) that may be used to support and protect buttress assemblies (100, 110). Cartridge (600) may also be used to easily load buttress assemblies (100, 110) on end effector (40). Cartridge (600) of this example includes a housing (610), a platform (620), and a plurality of retention members (652) that are configured to releasably secure buttress assemblies (100, 110) to platform (520) just like arms (252) or arms (352) described above. It should be understood that retention members (652) are provided by way of example only; and that cartridge (600) may instead include any other suitable kinds of buttress assembly (100, 110) retention features, including but not limited to those described elsewhere herein.

Platform (620) of the present example includes a plurality of protrusions (622) and a plurality of fins (624). In some versions, protrusions (622) and/or fins (624) are rigid. Protrusions (622) are in the form of an array of short, flat-topped pegs in the present example, though it should be understood that protrusions (622) may take a variety of alternative forms. Fins (624) are sized and arranged to fit in channel (62) of anvil (60). It should be understood that fins (624) may cooperate with the sidewalls defining channel (62) to ensure that anvil (60) is properly aligned with buttress assembly (100) as anvil (60) is closed down toward buttress assembly (100) and platform (620). It should also be understood that the underside of platform (620) (i.e., the side carrying buttress assembly (110), associated with staple cartridge (70)), may also include protrusions (622) and fins (624). Fins (624) on the underside of platform (620) may be sized and arranged to fit in channel (72) of staple cartridge (70). Moreover, as will be described in greater detail below, fins (624) on the underside of platform (620) may be configured to prevent cartridge (600) from being used with a staple cartridge (70) that has already been fired.

Figure 11A:
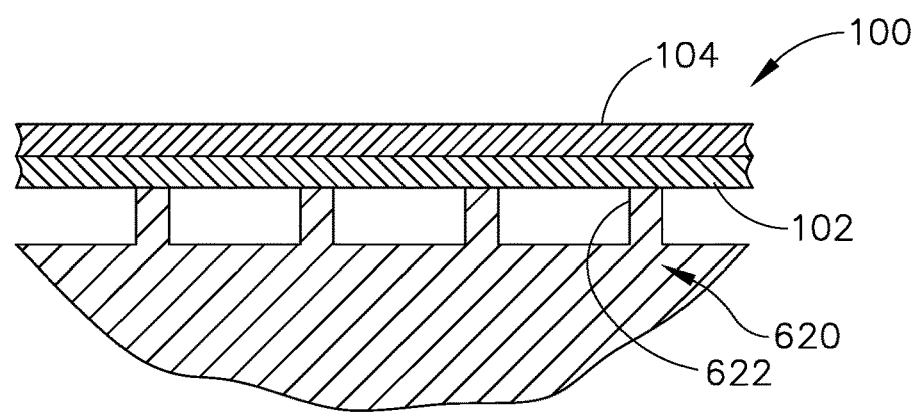
FIG. 11A depicts a partial, cross-sectional end view of a buttress assembly disposed on a platform of the buttress applier cartridge of FIG. 10.
Figure 11B:
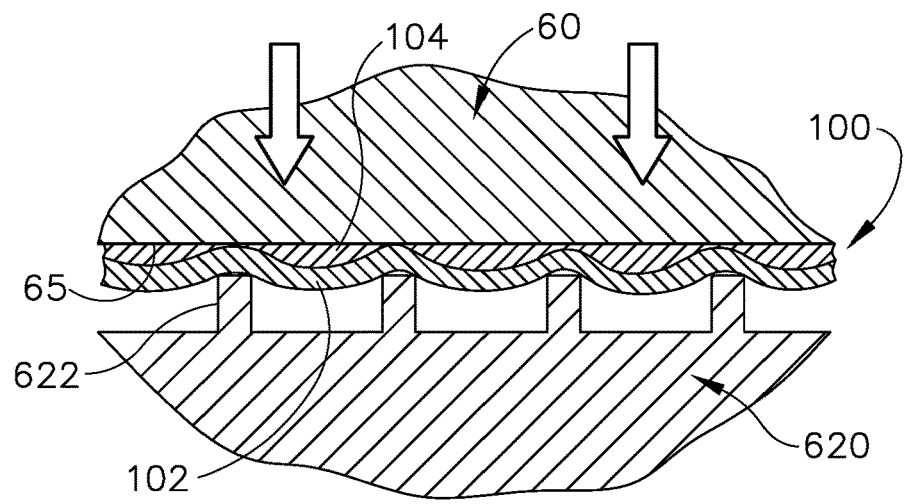
FIG. 11B depicts partial, cross-sectional end view of the buttress assembly and platform of FIG. 11A, with an anvil of the end effector of FIG. 2 pressing the buttress assembly against pressure applying features of the platform.
Figure 11C:
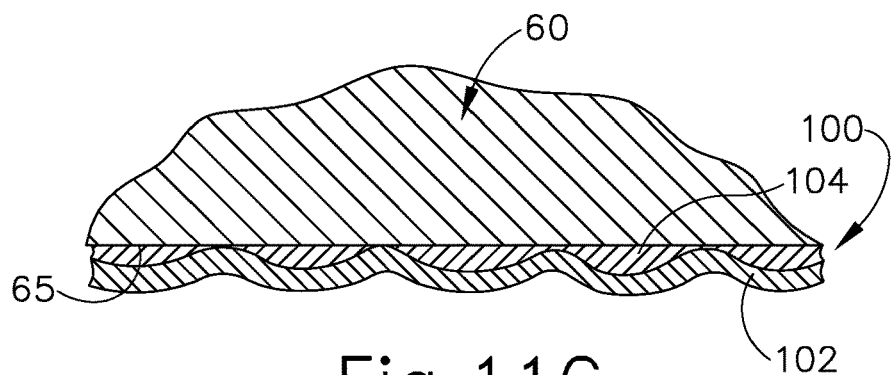
FIG. 11C depicts a partial, cross-sectional end view of the buttress assembly and anvil of FIG. 11B, with the buttress assembly adhered to the anvil.

As shown in FIG. 11A, protrusions (622) directly engage body (102) of buttress assembly (100), and thereby support buttress assembly (100) at a plurality of discrete locations along body (102). FIG. 11B shows anvil (60) clamping down on buttress assembly (100) and platform (620). As shown, protrusions (622) provide localized pressure on adhesive layer (104) against the underside (65) of anvil (60). This localization provides greater pressure at the regions associated with protrusions (622) than would otherwise be applied on adhesive layer (104) against the underside (65) of anvil (60) if platform (620) lacked protrusions (622). When anvil (60) is pulled away from platform (620) (e.g., when end effector (40) is returned to the open position), buttress assembly (100) is adhered to underside (65), with adhesion maximized at the locations associated with protrusions (622) as shown in FIG. 11C.

Figure 12A:
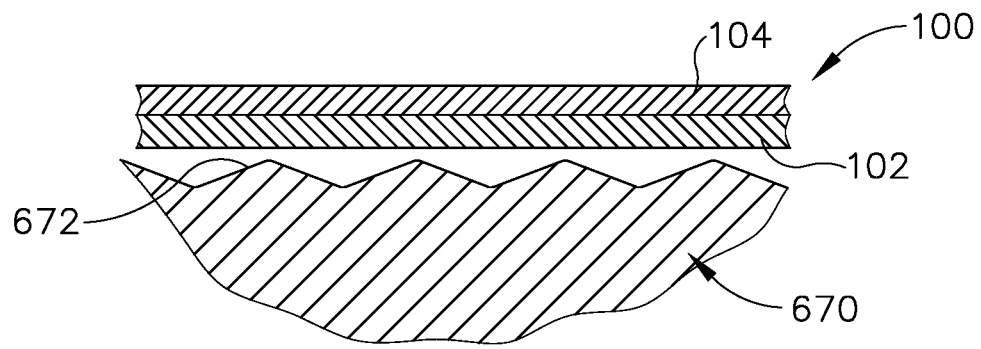
FIG. 12A depicts a partial, cross-sectional end view of a buttress assembly disposed on an exemplary variation of the platform of FIG. 11A.
Figure 12B:
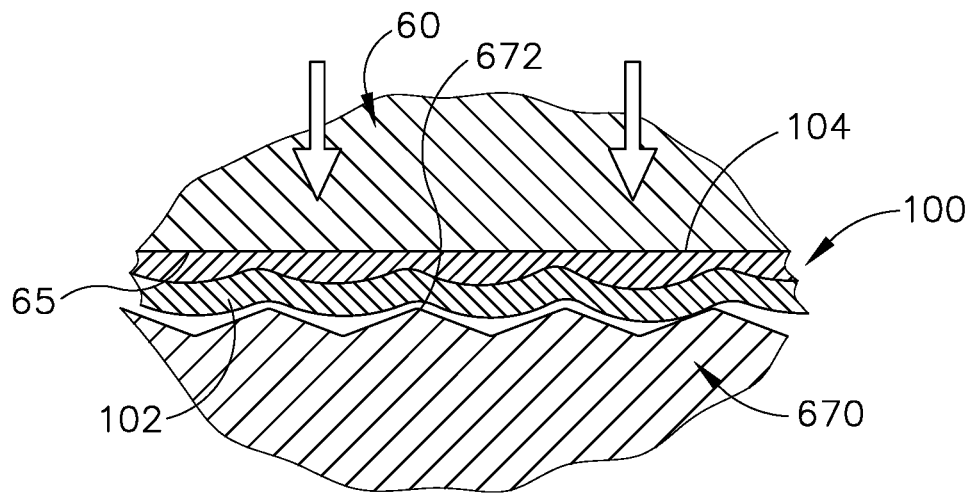
FIG. 12B depicts a partial, cross-sectional end view of the buttress assembly and platform of FIG. 12A, with an anvil of the end effector of FIG. 2 pressing the buttress assembly against pressure applying features of the platform.
Figure 12C:
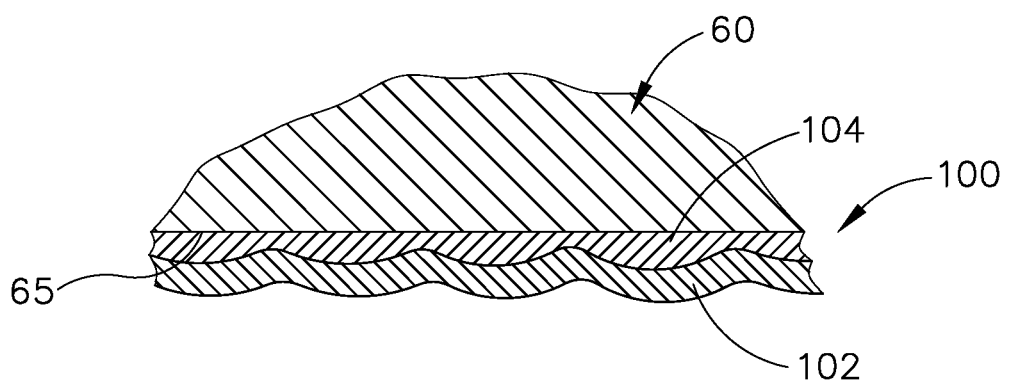
FIG. 12C depicts a partial, cross-sectional end view of the buttress assembly and anvil of FIG. 12B, with the buttress assembly adhered to the anvil.

FIGS. 12A-12C show another exemplary alternative platform (670) that may be readily incorporated into cartridge (600) in place of platform (620). Platform (670) of this example is substantially identical to platform (620) described above, except that platform (670) of this example has a surface geometry in the form of a triangular wave. In some versions, the triangular wave configuration extends along only one cross-sectional dimension, such that the peaks (672) of the triangular wave span across the entire width of platform (670) like ridges. In some other versions, the triangular wave configuration extends along two cross-sectional dimensions, such that the peaks (672) of the triangular wave form discrete points.

As shown in FIG. 12A, peaks (672) directly engage body (102) of buttress assembly (100), and thereby support buttress assembly (100) at a plurality of discrete locations along body (102). FIG. 12B shows anvil (60) clamping down on buttress assembly (100) and platform (670). As shown, peaks (672) provide localized pressure on adhesive layer (104) against the underside (65) of anvil (60). This localization provides greater pressure at the regions associated with peaks (672) than would otherwise be applied on adhesive layer (104) against the underside (65) of anvil (60) if platform (670) lacked peaks (672). When anvil (60) is pulled away from platform (670) (e.g., when end effector (40) is returned to the open position), buttress assembly (100) is adhered to underside (65), with adhesion maximized at the locations associated with peaks (672) as shown in FIG. 12C.

It should be understood that the cylindraceous peg configuration of protrusions (622) and the triangular wave peak configuration of peaks (672) are merely illustrative examples. Other features and surface geometries that may be incorporated into a platform to provide localized pressure will be apparent to those of ordinary skill in the art in view of the teachings herein.

Figure 13:
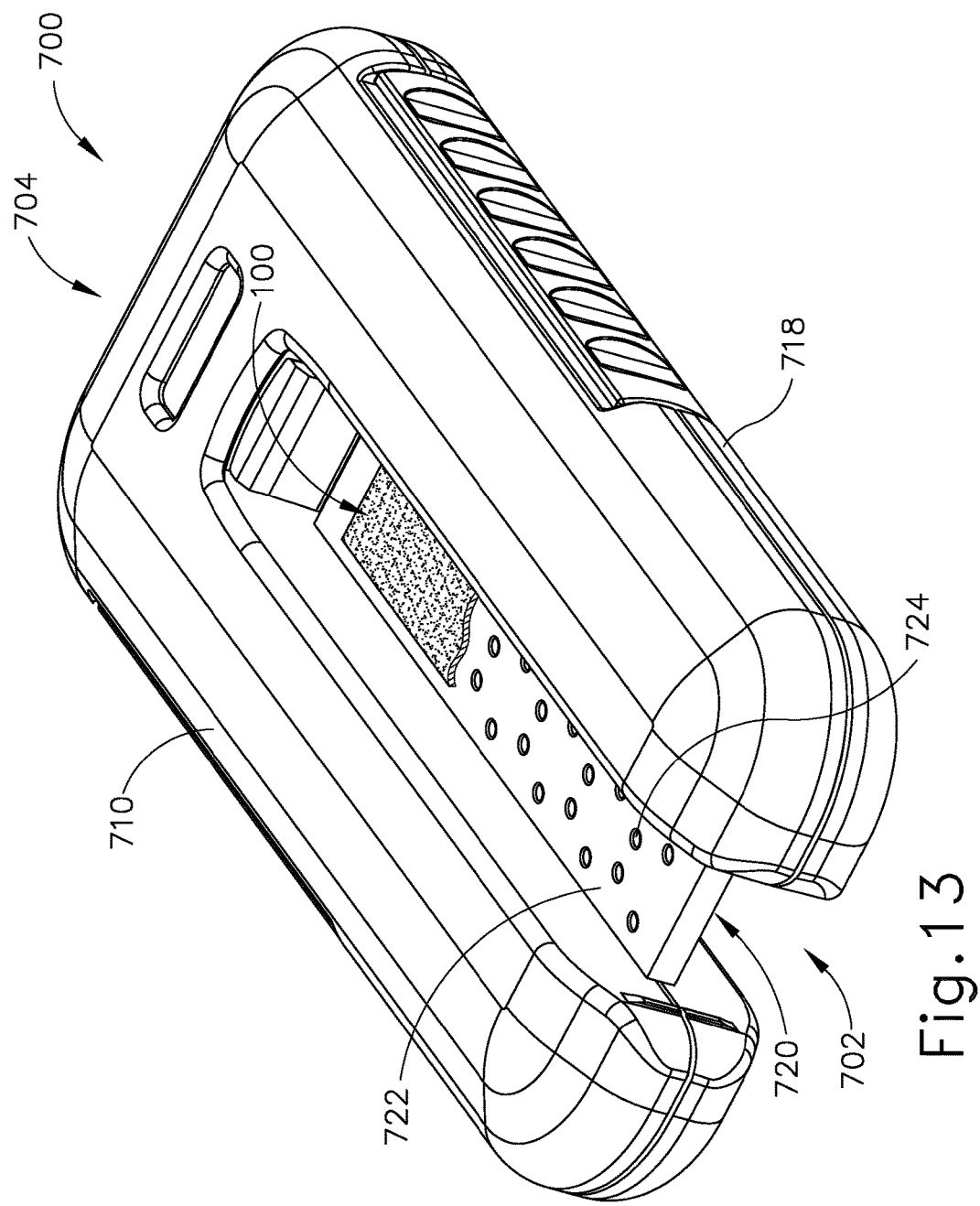
FIG. 13 depicts a perspective view of another exemplary buttress applier cartridge that may be used to carry and apply the buttress assembly of FIG. 5A.

B. Exemplary Buttress Applier Cartridge with Platform Having Regions of Varying Compression Characteristics FIG. 13 shows another exemplary alternative buttress applier cartridge (700) that may be used to support and protect buttress assemblies (100, 110). Cartridge (700) may also be used to easily load buttress assemblies (100, 110) on end effector (40). Cartridge (700) of this example comprises an open end (702) and a closed end (704). Open end (702) is configured to receive end effector (40) as described above. Cartridge (700) further includes a first housing (710) and a second housing (718), which each generally define a "U" shape to present open end (402). A platform (720) is interposed between housings (710, 718).

In some versions, buttress assemblies (100, 110) are adhered to platform (720). By way of example only, buttress assemblies (100, 110) may be adhered to platform (720) using the same adhesive material that is used to adhere buttress assemblies (100, 110) to underside (65) of anvil (60) and deck (73) of staple cartridge (70). In some such versions, the sides of buttress assemblies (100, 110) that are adhered to platform (720) include less adhesive material than the amount of adhesive material that is used to adhere buttress assemblies (100, 110) to underside (65) of anvil (60) and deck (73) of staple cartridge (70), to thereby promote release of buttress assemblies (100, 110) from platform (720) when buttress assemblies (100, 110) are adhered to underside (65) of anvil (60) and deck (73) of staple cartridge (70). For instance, the adhesive may be provided in only discrete portions (e.g., in a pattern) along the sides of buttress assemblies (100, 110) that are adhered to platform (720).

Platform (720) of the present example comprises a body (722) and an array of resilient assemblies (724). Body (722) of the present example is compressible; and resilient assemblies (724) are also compressible. However, body (722) is configured to maintain a generally compressed configuration after being compressed then released; while resilient assemblies (724) are configured to generally return to a non-compressed configuration after being compressed then released. In addition, during compression of platform (720), the resilience of resilient assemblies (724) will provide a greater outward resistance on whatever is compressing platform (720) than the outward resistance provided by body (722) of platform (720). By way of example only, each resilient assembly (724) may comprise a coil spring in a sheath; and resilient assemblies (724) may be snugly fit in respective undersized openings of body (722). Other suitable forms that resilient assemblies (724) may take will be apparent to those of ordinary skill in the art in view of the teachings herein. It should also be understood that a variety of materials and configurations may be used to form body (722), including but not limited to a viscous foam material.

FIGS. 14A-14C show a sequence where buttress assemblies (100, 110) and platform (720) are compressed and released by end effector (40). In this example, buttress assembly (100) is modified to include several integral, discrete protrusions (106) projecting downwardly from body (102). Similarly, buttress assembly (110) is modified to include several integral, discrete protrusions (116) projecting upwardly from body (102). Protrusions (106, 116) may be rigid or semi-rigid. By way of example only, protrusions (106, 116) may be shaped like short, cylindraceous pegs. Alternatively, protrusions (106, 116) may have any other suitable configuration.

At the stage shown in FIG. 14A, before end effector (40) is clamped down on buttress assemblies (100, 110) and platform (720), the upper and lower surfaces of body (722) are flush with the upper and lower ends of resilient assemblies (724), such that the upper and lower surfaces of platform (720) are substantially flat. Buttress assemblies (100, 110) are supported on platform (720) via protrusions (106, 116). In the present example, protrusions (106, 116) and resilient assemblies (724) are positioned and arranged such that protrusions (106, 116) do not engage the ends of any of resilient assemblies (724). In other words, protrusions (106, 116) only engage body (722) of platform (720).

FIG. 14B shows end effector (40) clamping down on where buttress assemblies (100, 110) and platform (720). As shown, protrusions (106, 116) engage body (722) to maximize compression of body (722) relative to resilient assemblies (724). Resilient assemblies (724) bear directly on bodies (102, 112) of buttress assemblies (100, 110), providing localized pressure similar to that provided protrusions (622) as described above. Thus, resilient assemblies (724) simultaneously enhance adhesion of adhesive layer (104) to underside (65) and adhesion of adhesive layer (114) to deck (73).

FIG. 14C shows end effector (40) returning to an open position, carrying buttress assemblies (100, 110) away from platform (720). Platform (720) is thus no longer being compressed by end effector (40). Nevertheless, body (722) maintains a substantially compressed configuration; while resilient assemblies (724) return to a generally uncompressed configuration. Buttress assemblies (100, 110) remain adhered to end effector (40), with enhanced adhesion provided by resilient assemblies (724), such that end effector (40) with buttress assemblies (100, 110) may be used to perform a surgical procedure as described above. It should be understood that body (722) does not necessarily need to maintain a substantially compressed configuration at the stage shown in FIG. 14C. In other words, body (722) may provide some degree of resilience. However, in versions where body (722) is resilient, the resilience of resilient assemblies (724) may be stronger than the resilience of body (722), such that resilient assemblies (724) may effectively provide localized concentrations of pressure against buttress assemblies (100, 110) when end effector (40) is closed upon buttress assemblies (100, 110) and platform (720).

FIGS. 15A-31C show another exemplary alternative platform (770) that may be readily incorporated into cartridge (700) or any other buttress applier cartridge described herein. As with platform (720) described above, buttress assemblies (100, 110) may be adhered to platform (770) in some versions. Platform (770) of this example comprises a body (772) with a plurality of resilient members (774) disposed in body (772). Body (772) of the present example is compressible; and resilient members (774) are also compressible. However, body (772) is configured to maintain a generally compressed configuration after being compressed then released (or at least take longer to return to the non-compressed configuration); while resilient members (774) are configured to generally return to a non-compressed configuration after being compressed then released (or return to the non-compressed configuration faster than body (772)). In other words, body (772) has a greater viscosity than resilient members (774). In addition, during compression of platform (770), the resilience of resilient members (774) will provide a greater outward resistance on whatever is compressing platform (770) than the outward resistance provided by body (772) of platform (770). By way of example only, each resilient member (774) may comprise a cylinder of material that has a greater density than the material forming body (772). In some versions, resilient members (774) and body (772) are formed of the same foam material; yet the foam material forming resilient members (774) has a greater density than the foam material forming body (772). Other suitable forms that resilient members (724) may take will be apparent to those of ordinary skill in the art in view of the teachings herein.

At the stage shown in FIG. 15A, before end effector (40) is clamped down on buttress assemblies (100, 110) and platform (770), the upper and lower surfaces of body (772) are flush with the upper and lower ends of resilient assemblies (774), such that the upper and lower surfaces of platform (770) are substantially flat. Buttress assemblies (100, 110) are supported flatly on platform (770). In some variations, buttress assemblies (100, 11) include protrusions (106, 116) when used with platform (770).

FIG. 15B shows end effector (40) clamping down on where buttress assemblies (100, 110) and platform (770). As shown, resilient members (774) bear directly on bodies (102, 112) of buttress assemblies (100, 110), providing localized pressure similar to that provided protrusions (622) as described above. Thus, resilient members (774) simultaneously enhance adhesion of adhesive layer (104) to underside (65) and adhesion of adhesive layer (114) to deck (73).

FIG. 15C shows end effector (40) returning to an open position, carrying buttress assemblies (100, 110) away from platform (770). Platform (770) is thus no longer being compressed by end effector (40). Nevertheless, body (772) maintains a substantially compressed configuration; while resilient members (774) return to a generally uncompressed configuration. Buttress assemblies (100, 110) remain adhered to end effector (40), with enhanced adhesion provided by resilient members (774), such that end effector (40) with buttress assemblies (100, 110) may be used to perform a surgical procedure as described above. It should be understood that body (772) does not necessarily need to maintain a substantially compressed configuration at the stage shown in FIG. 15C. However, in versions where body (772) is resilient, the resilience of resilient members (774) may be stronger than the resilience of body (772), such that resilient members (774) may effectively provide localized concentrations of pressure against buttress assemblies (100, 110) when end effector (40) is closed upon buttress assemblies (100, 110) and platform (770).

Figure 16:
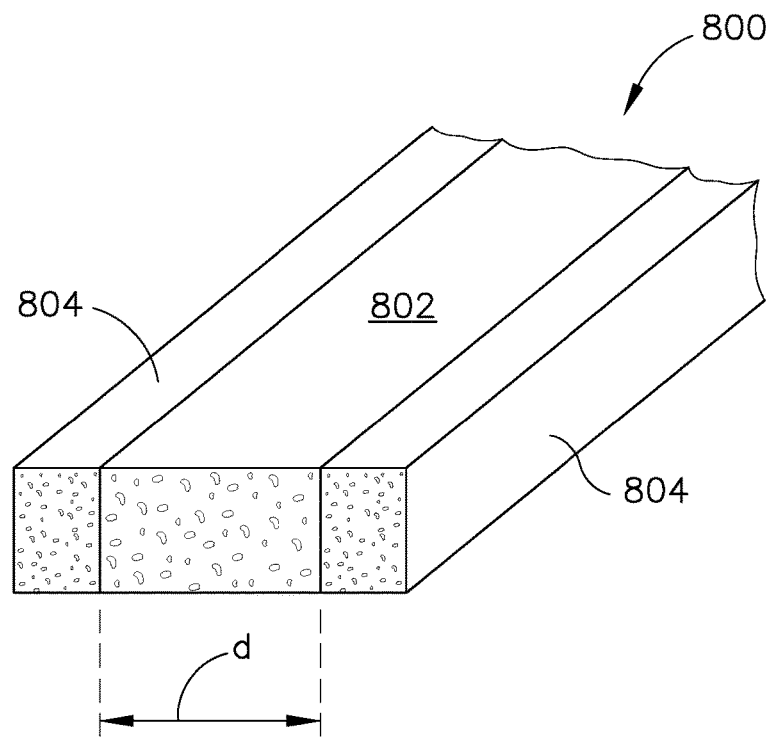
FIG. 16 depicts a partial perspective view of an exemplary alternative platform that may be incorporated into a buttress applier cartridge.

FIG. 16 shows yet another exemplary alternative platform (800) that may be readily incorporated into cartridge (700) or any other buttress applier cartridge described herein. Platform (800) of this example comprises a first longitudinally extending body zone (802) and a pair of second longitudinally extending body zones (804). Body zones (804) extend longitudinally along both lateral sides of body zone (802) and are laterally separated by a distance (d). Body zones (804) are sized and positioned to correspond with the lateral outermost regions of underside (65) of anvil (60) and deck (73) of staple cartridge (70). In some versions, all body zones (802, 804) are compressible but body zone (802) has a durometer that is different from the durometer of body zones (804). For instance, in some versions body zone (802) is configured to maintain a generally compressed configuration after being compressed then released while body zones (804) are configured to generally return to a non-compressed configuration after being compressed then released. In addition, during compression of platform (800), the resilience of body zones (804) will provide a greater outward resistance on whatever is compressing platform (800) than the outward resistance provided by body zone (802) of platform (800). By way of example only, each body zone (804) may comprise a material that has a greater density than the material forming zone (802). In some versions, body zones (804) and body zone (802) are formed of the same foam material; yet the foam material forming body zones (804) has a greater density than the foam material forming body zone (802). Other suitable forms that body zones (804) may take will be apparent to those of ordinary skill in the art in view of the teachings herein.

Before end effector (40) is clamped down on buttress assemblies (100, 110) and platform (800), the upper and lower surfaces of body zone (802) are flush with the upper and lower ends of body zones (804), such that the upper and lower surfaces of platform (800) are substantially flat. Buttress assemblies (100, 110) are supported flatly on platform (800). When end effector (40) clamps down on where buttress assemblies (100, 110) and platform (800) as described above, body zones (804) bear directly on bodies (102, 112) of buttress assemblies (100, 110), providing localized pressure along the lateral outermost regions of underside (65) of anvil (60) and deck (73) of staple cartridge (70). Thus, body zones (804) simultaneously enhance adhesion of adhesive layer (104) to underside (65) and adhesion of adhesive layer (114) to deck (73).

After end effector (40) returns to an open position, carrying buttress assemblies (100, 110) away from platform (800), body zone (802) may maintain a substantially compressed configuration; while body zones (804) return to a generally uncompressed configuration. Buttress assemblies (100, 110) remain adhered to end effector (40), with enhanced adhesion provided by body zones (804), such that end effector (40) with buttress assemblies (100, 110) may be used to perform a surgical procedure as described above. It should be understood that body zone (802) does not necessarily need to maintain a substantially compressed configuration after end effector (40) returns to an open position. However, in versions where body zone (802) is resilient, the resilience of body zones (804) may be stronger than the resilience of body zone (802), such that body zones (804) may effectively provide localized concentrations of pressure against buttress assemblies (100, 110) when end effector (40) is closed upon buttress assemblies (100, 110) and platform (800).

C. Exemplary Buttress Applier Cartridge with Platform Having Varying Thickness

Figure 17:
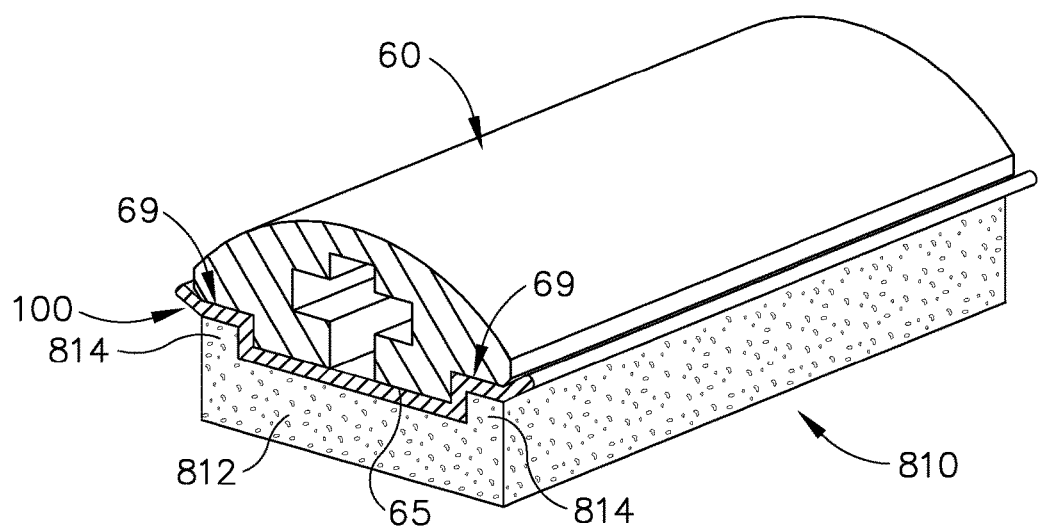
FIG. 17 depicts a partial perspective view of the anvil of the end effector of FIG. 2 compressing a buttress against another exemplary alternative platform that may be incorporated into a buttress applier cartridge.

In addition to or as an alternative to modifying a platform to include surface features or resilient features that provide enhanced pressure in localized regions, it may be desirable to provide a buttress applier cartridge with a platform that has varying thickness to enhance or otherwise promote adhesion between buttress assemblies (100, 110) and end effector (40). For instance, FIG. 17 shows an exemplary platform (810) that may be readily incorporated into cartridge (700) or any other buttress applier cartridge described herein. Platform (810) of this example comprises a longitudinally extending thin region (812) that is flanked by longitudinally extending thick regions (814). In the present example, platform (810) is a single, homogenous continuum of material that is formed to include regions (812, 814). In some other versions, regions (814) are initially formed separately from region (812) and are then joined to regions (812) to form an integral unit.

As shown in FIG. 17, thick regions (814) are configured to complement recessed regions (69) on underside (65) of anvil (60). Regions (812, 814) thus cooperate to ensure that buttress assembly (100) is applied with uniform pressure along the full width of underside (65), including recessed regions (69). It should be understood that, if platform (810) instead had a uniform thickness across the width of platform (810) (e.g., lacking thick regions (814)), buttress assembly (100) may not be adhered as well to recessed regions (69) on underside (65) of anvil (60).

Figure 18:
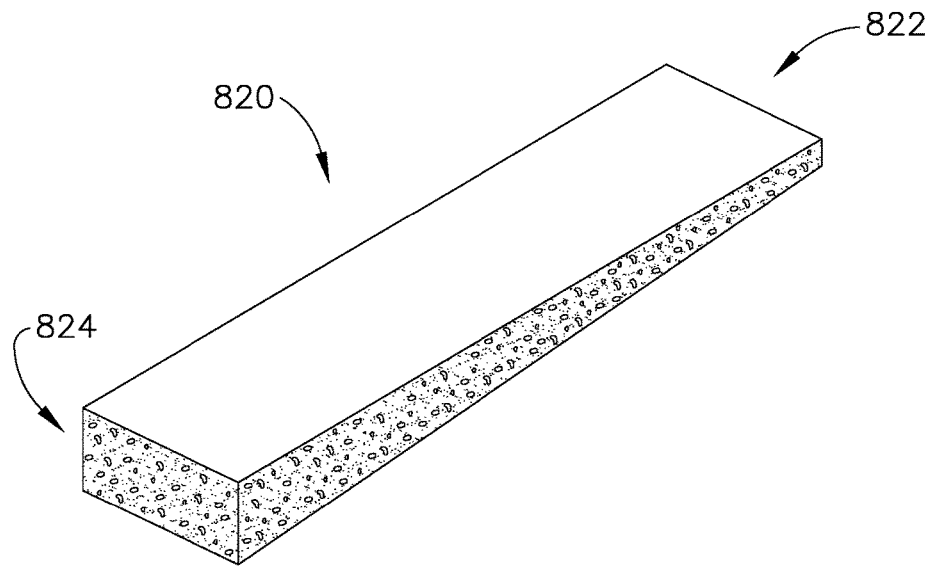
FIG. 18 depicts a perspective view of another exemplary alternative platform that may be incorporated into a buttress applier cartridge.

While the thickness of platform (810) varies along the width of platform (810), it may also be desirable to vary the thickness of a platform along the length of the platform. FIG. 18 shows yet another exemplary platform (820) that may be readily incorporated into cartridge (700) or any other buttress applier cartridge described herein. Platform (820) of this example is tapered along the length of platform (820). In particular, the proximal end (822) of platform (820) is thinner than the distal end (824) of platform (820). When a buttress applier cartridge incorporating platform (820) is positioned in an open end effector (40), proximal end (822) would be positioned closer to the pivot region between anvil (60) and lower jaw (50), and distal end (824) would be positioned closer to the distal ends of anvil (60) and staple cartridge (70).

The tapered profile of platform (820) may complement the closure profile of anvil (60) as anvil (60) is clamped down onto a buttress assembly (100) on platform (820). In particular, as anvil (60) is closed toward lower jaw (50) and staple cartridge (70), anvil (60) may define an acute angle with lower jaw (50) and staple cartridge (70) up until anvil (60) reaches a fully closed position. Once anvil (60) reaches a fully closed position, anvil (60) may be parallel with lower jaw (50) and staple cartridge (70). If an operator fails to fully close anvil (60) when the operator is attempting to adhere a buttress assembly (100) to underside (65), the increased thickness at the distal end (824) of platform (820) may increase the likelihood of successful adhesion in the distal regions of underside (65) and buttress assembly (100) even though anvil (60) never achieves a fully parallel orientation with respect to lower jaw (50) and staple cartridge (70).

Figure 19:
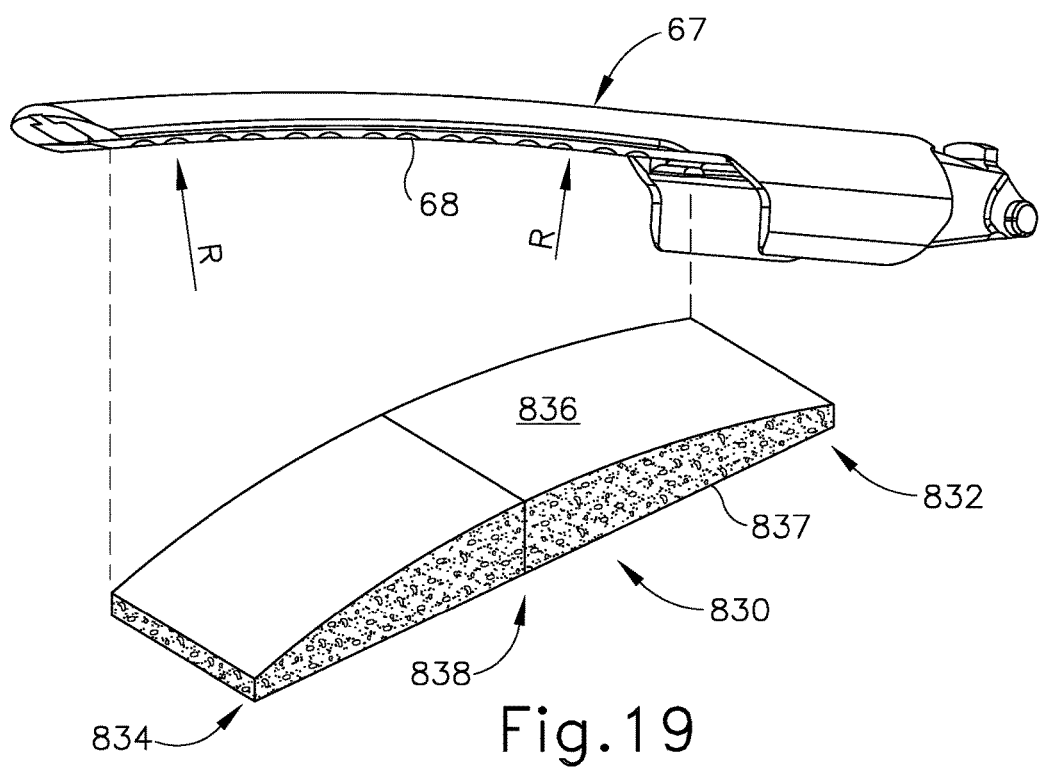
FIG. 19 depicts a perspective view of another exemplary alternative platform that may be incorporated into a buttress applier cartridge, with an exemplary alternative curved anvil positioned over the platform.

FIG. 19 shows yet another exemplary platform (830) that may be readily incorporated into cartridge (700) or any other buttress applier cartridge described herein. Platform (830) of this example has a relatively thin proximal end (832) and distal end (834), with a relatively thick central region (838). Platform (830) has a flat lower surface (837) and a convex upper surface (836). Flat lower surface (837) is configured to complement the generally flat surface of deck (73) of staple cartridge (70). Convex upper surface (836) is configured to complement a curved anvil (67). Anvil (67) of this example is substantially identical to anvil (60) described above and may be readily incorporated into end effector (40). However, anvil (67) of this example has a slightly curved underside (68). In some versions, the radius of curvature of convex upper surface (836) complements the radius of curvature of underside (68), thereby ensuring that a buttress assembly (100) that is disposed on convex upper surface (836) will be adhered to underside (68) with uniform pressure along the full length of underside (68). It should be understood, however, that convex upper surface (836) may have a radius of curvature that is less than the radius of curvature of underside (68). Similarly, platform (830) may be used with an anvil (60) that has a substantially flat underside (68). In such versions, the curvature of convex upper surface (836) may force contact between buttress assembly (100) at the longitudinal center of underside (65) of anvil (60) first; and apply the most pressure to the longitudinal center of underside (65) of anvil (60) to ensure maximum fixation of buttress assembly (100) at the longitudinal center of underside (65) of anvil (60). This may minimize the risk of buttress assembly (100) slipping along underside (65) of anvil (60) during manipulation of tissue or placement of anvil (60) on tissue.

Other suitable ways in which the thickness of a platform may be varied along the width and/or length of the platform will be apparent to those of ordinary skill in the art in view of the teachings herein.

V. EXEMPLARY ALTERNATIVE BUTTRESS RETENTION FEATURES FOR BUTTRESS APPLIER CARTRIDGES

As described above, a cartridge (200) may secure buttress assemblies (100, 110) to platform (220) using arms (252). However, it will be understood that arms (252) are merely illustrative examples of structures that may be used to secure buttress assemblies (100, 110) to platform (220). Several additional structures that may be used to secure buttress assemblies (100, 110) to platform (220) will be described in greater detail below, while still further examples will be apparent to those of ordinary skill in the art in view of the teachings herein. It should be understood that the following teachings may be readily incorporated into any of the various buttress applier cartridges described herein.

A. Exemplary Buttress Retention Features Integrated into Platform of Buttress Applier Cartridge In cartridge (200) described above, buttress assemblies (100, 110) are secured to platform (220) using features positioned along the outward lateral edges of buttress assemblies (100, 110). In particular, arms (252) secure buttress assemblies (100, 110) in cartridge (200). In addition to or as an alternative to using these kinds of features to secure buttress assemblies (100, 110) to a platform, it may be desirable to incorporate features directly into a platform that secure buttress assemblies (100, 110) to the platform. The following provides merely illustrative examples of how a platform may include integral features that releasably secure buttress assemblies (100, 110) to the platform. Other suitable variations will be apparent to those of ordinary skill in the art in view of the teachings herein.

1 Exemplary Platform with Integral, Collapsible Retainer Posts

Figure 20:
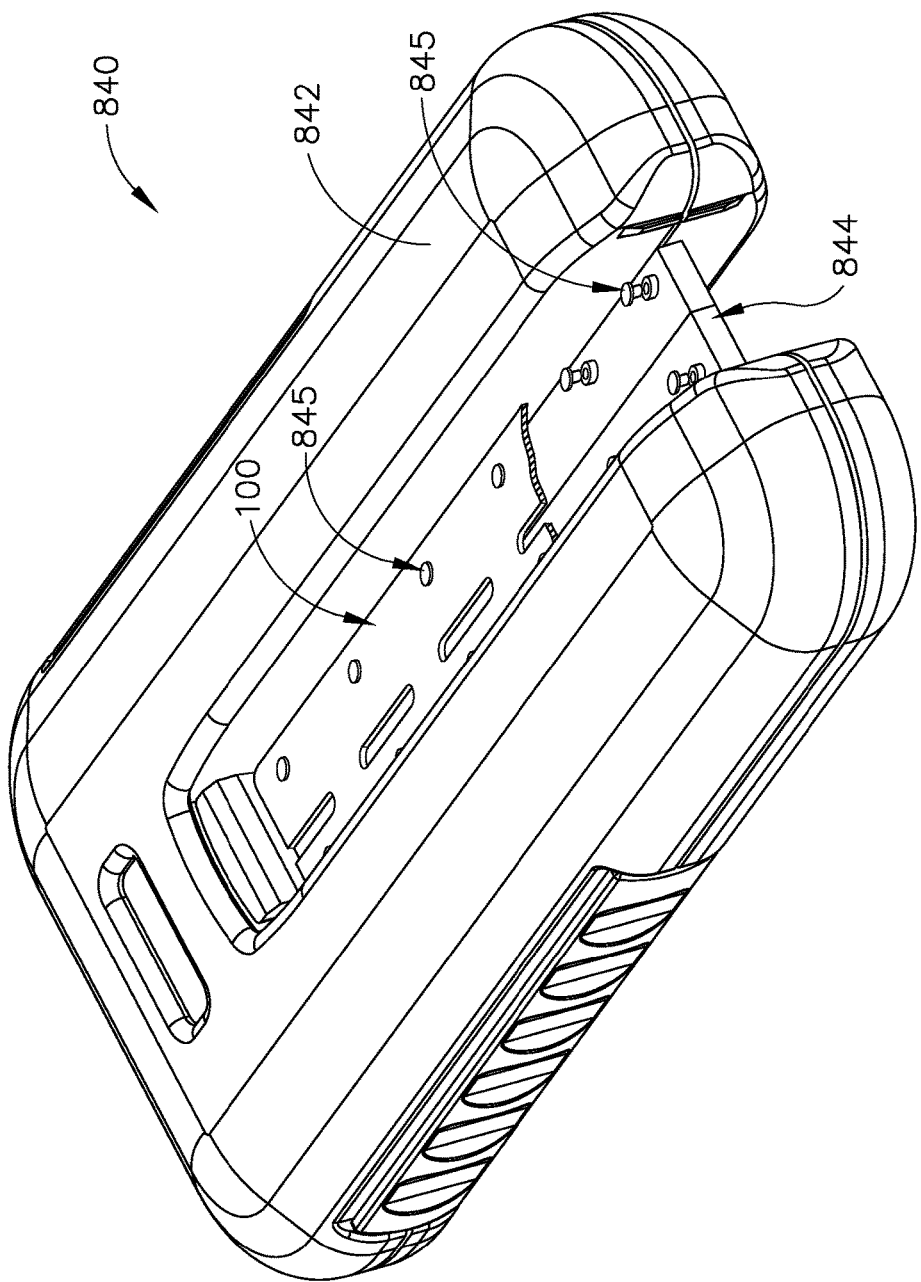
FIG. 20 depicts a partial perspective view of an open end of another exemplary buttress applier cartridge that may be used to carry and apply the buttress assembly of FIG. 5A.

FIG. 20 shows an exemplary alternative buttress applier cartridge (840) that may be used to support and protect buttress assemblies (100, 110). Cartridge (840) may also be used to easily load buttress assemblies (100, 110) on end effector (40). Cartridge (840) of this example includes a housing (842) and a platform (844). Platform (844) of this example is substantially identical to platforms (220) described above, except that platform (844) of this example includes fastener assemblies (845). Fastener assemblies (845) extend through the thickness of platform (844) and buttress assemblies (100, 110); and are arranged in an array such that fastener assemblies (845) are generally equidistantly spaced from each other along the surfaces of buttress assemblies (100, 110). As described in further detail below, fastener assemblies (845) releasably secure buttress assemblies (100, 110) to platform (845). In the present example, cartridge (840) lacks arms (252). In some other versions, fastener assemblies (845) are provided as a supplement to arms (252). It should therefore be understood that fastener assemblies (845) may be used in combination with other features such as arms (252).

Figure 21A:
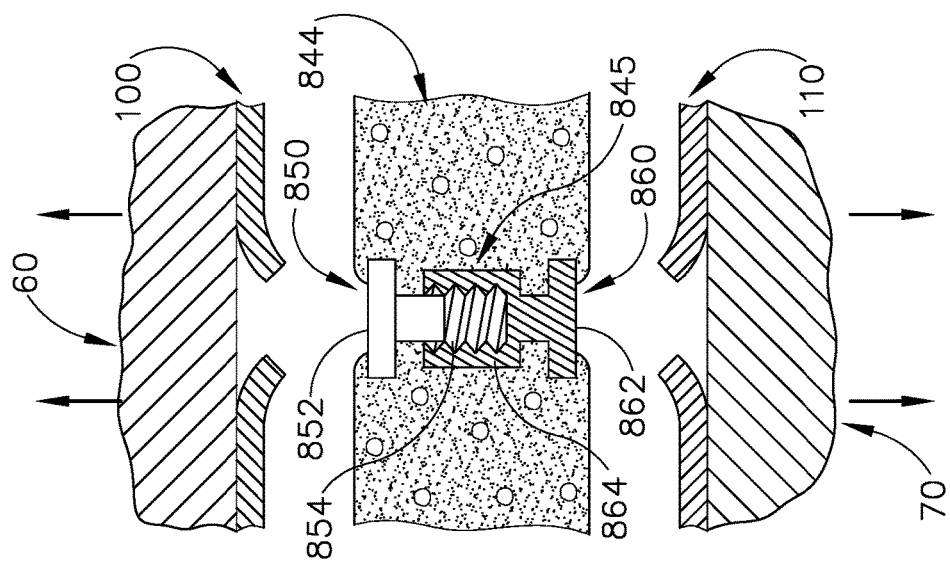
FIG. 21A depicts a partial, cross-sectional end view of a platform and buttress assembly of the buttress applier cartridge of FIG. 20, with a retention post assembly in a non-collapsed state.
Figure 21B:
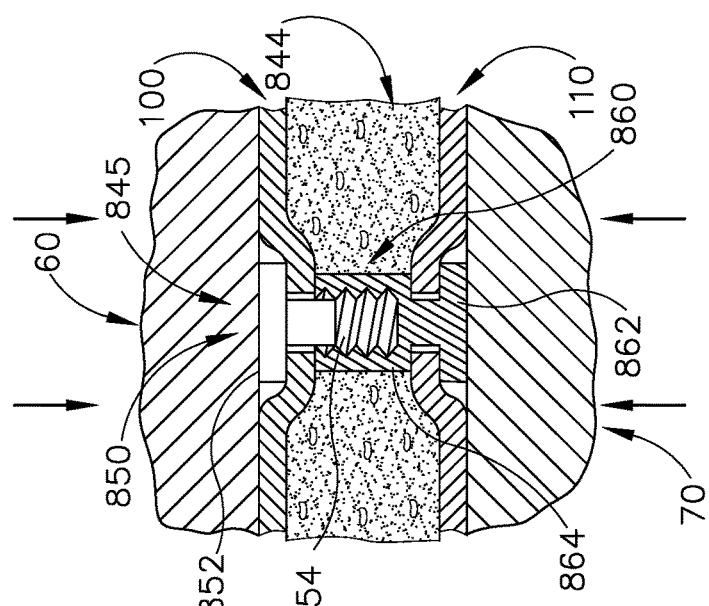
FIG. 21B depicts a partial, cross-sectional end view of the platform and buttress assembly of FIG. 21A, with the end effector of FIG. 2 compressing the platform and buttress assembly, thereby transitioning the retention post assembly to a collapsed state.
Figure 21C:
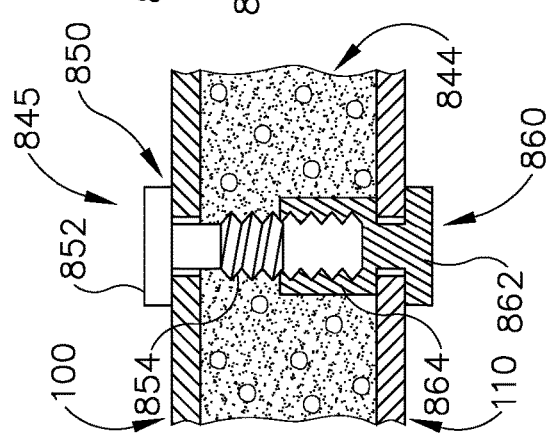
FIG. 21C depicts a partial, cross-sectional end view of the platform and buttress assembly of FIG. 21A, with the end effector in an open configuration, with the buttress assembly adhered to the end effector, and with the retention post assembly remaining in a collapsed state in the platform.

As best seen in FIGS. 21A-21C, each fastener assembly (845) comprises a male member (850) and a female member (860). Male member (850) comprises a head (852) and a shank (854) extending downwardly from head (852). Head (852) is positioned on top of buttress assembly (100). Head (852) is sized and configured to releasably hold buttress assembly (100) on platform (844). Shank (854) extends through buttress assembly (100) and platform (844). Shank (854) includes a longitudinally spaced array of annular ridges or barbs. Female member (860) comprises a head (862) and a shank (864) extending upwardly from head (862). Head (862) is positioned below buttress assembly (110). Head (862) is sized and configured to releasably hold buttress assembly (110) on platform (844). Shank (864) extends through buttress assembly (110) and platform (844). Shank (864) includes a recess that includes a longitudinally spaced array of interior annular ridges or barbs. These interior features of shank (864) are configured to complement the exterior features of shank (854).

FIG. 21A shows platform (844), fastener assemblies (845), and buttress assemblies (100, 110) prior to engagement with end effector (40). As shown, shanks (854, 864) are separated from each other. Shanks (854, 864) nevertheless provide enough friction with the material of platform (844) to cooperate with heads (852, 862) in such a way that fastener assemblies (845) secure buttress assemblies (100, 110) to platform (844).

FIG. 21B shows platform (844), fastener assemblies (845), and buttress assemblies (100, 110) being clamped by a closed end effector (40). As shown, closure of end effector (40) compresses platform (844), thereby driving members (850, 860) into engagement with each other. In particular, shank (854) enters shank (864), reducing the effective height of fastener assembly (845). The exterior ridges or barbs of shank (854) ratchetingly engage the complementary interior features of shank (864), thereby fixedly securing members (850, 860) together. At this stage, adhesive layers (102, 112) (not shown in FIG. 21B) secure buttress assemblies (100, 110) to anvil (60) and staple cartridge (70), respectively.

FIG. 21C shows platform (844), fastener assemblies (845), and buttress assemblies (100, 110) after being released by the clamped end effector (40). As shown, members (850, 860) remain engaged with each other due to the engagement between the exterior ridges or barbs of shank (854) and the complementary interior features of shank (864). Platform (844) has self-expanded back to a non-compressed state. Buttress assemblies (100, 110) remain secured to anvil (60) and staple cartridge (70), respectively. During the transition from the stage shown in FIG. 21B to the stage shown in FIG. 21C, heads (852, 862) have torn through buttress assemblies (100, 110). Buttress assemblies (100, 110) are thus released from platform (844) while fastening assemblies (845) remain engaged with platform (844). End effector (40) is then ready for use in a surgical procedure as described above.

2. Exemplary Platform with Integral, Frangible Retainer Stems

FIGS. 22A-22C show another exemplary platform (870) and fastening assembly (880) that may be used in lieu of platform (844) and fastening assembly (845) described above. It should be understood that platform (870) may include an array of fastening assemblies (880), just like platform (844) including an array of fastening assemblies (845) as described above. It should also be understood that platform (870) and fastening assembly (880) may be used in any of the cartridges described herein, with or without additional fastening features such as arms (252), etc.

Fastening assembly (880) of the present example comprises a first head (882), a second head (884), and a frangible stem (886) extending between heads (882, 884). Head (882) is positioned above buttress assembly (100) and is configured to hold buttress assembly (100) on platform (870). Head (884) is positioned below buttress assembly (110) and is configured to hold buttress assembly (110) on platform (870). Stem (886) passes through buttress assemblies (100, 110) and platform (870) to secure heads (882, 884) together. It should therefore be understood that heads (882, 884) and stem (886) cooperate to secure buttress assemblies (100, 110) to platform (870).

FIG. 22A shows platform (870), fastener assembly (880), and buttress assemblies (100, 110) prior to engagement with end effector (40). FIG. 22B shows platform (870), fastener assembly (880), and buttress assemblies (100, 110) being clamped by a closed end effector (40). As shown, closure of end effector (40) compresses platform (870), thereby heads (882, 884) toward each other. This causes stem (864) to fracture. At this stage, adhesive layers (102, 112) (not shown in FIG. 22B) secure buttress assemblies (100, 110) to anvil (60) and staple cartridge (70), respectively.

FIG. 22C shows platform (870), fastener assembly (880), and buttress assemblies (100, 110) after being released by the clamped end effector (40). As shown, platform (870) has self-expanded back to a non-compressed state. Buttress assemblies (100, 110) remain secured to anvil (60) and staple cartridge (70), respectively. Heads (882, 884) remain captured between buttress assemblies (100, 110) remain secured to anvil (60) and staple cartridge (70), respectively. Fractured stem (864) remains disposed in platform (870). During the transition from the stage shown in FIG. 22B to the stage shown in FIG. 22C, friction between the material of stem (864) and platform (870) provides a firm enough grip on stem (864) such that the portions of stem (864) that were initially positioned in platform (870) (i.e., at the stage shown in FIG. 22A) remain in platform (870). In other words, stem (864) will fracture at least once during closure of end effector (40) (FIG. 22A to FIG. 22B); and fracture at least one more time during opening of end effector (40) (FIG. 22B to FIG. 22C). It should be understood that, at the stage shown in FIG. 22C, buttress assemblies (100, 110) are fully secured to end effector (40). End effector (40) is then ready for use in a surgical procedure as described above.

B. Exemplary Buttress Applier Cartridge with Retainers Disposed Over Platform

Figure 23:
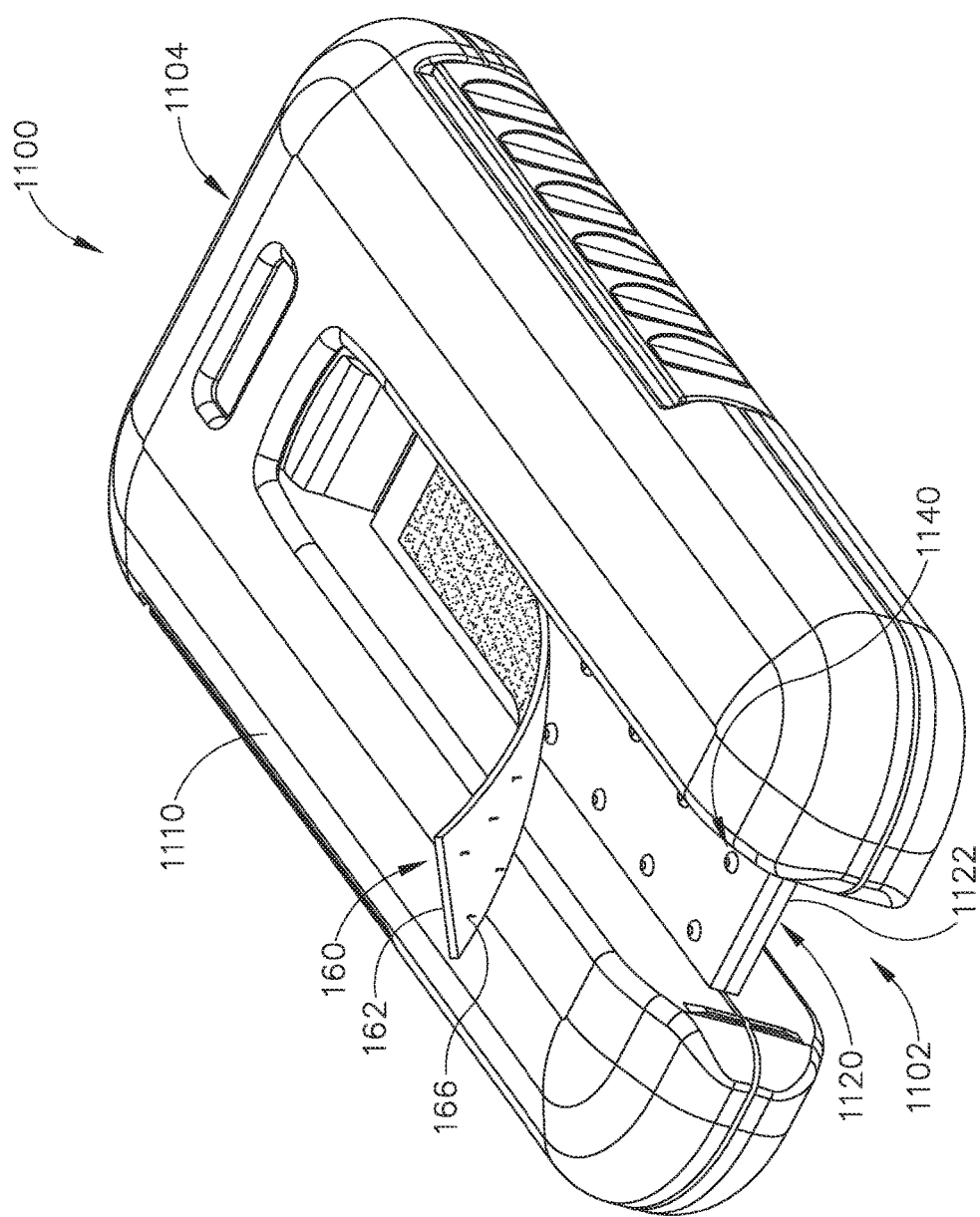
FIG. 23 depicts a perspective view of another exemplary alternative buttress applier cartridge.

FIG. 23 shows yet another exemplary alternative buttress applier cartridge (1100) that may be used to support and protect one or more buttress assemblies (160). Cartridge (1100) may also be used to easily load one or more buttress assemblies (160) on end effector (40). Cartridge (1100) of this example includes an open end (1102) and a closed end (1104) defined by a housing (1110). Cartridge (1100) further includes and a platform (1120) supporting a buttress assembly (160). While only one buttress assembly (160) is shown in FIG. 23, it should be understood that a mirror image buttress assembly (160) may be provided on the underside of platform (1120), such that cartridge (1100) may carry upper and lower buttress assemblies (160) just like other buttress applier cartridges carry buttress assemblies (100, 110) in other examples described herein. Alternatively, cartridge (1100) may be configured to support and release only one buttress assembly (160). In such versions, the single buttress assembly (160) may be configured to be applied to underside (65) of anvil (60) or deck (73) of staple cartridge (70).

Platform (1120) of the present example comprises a body (1122) and a plurality of retainers (1140) positioned on body (1122). Retainers (1140) are arranged in an array such that retainers (1140) are generally equidistantly spaced from each other along the surfaces of buttress assembly (160). As described in further detail below, retainers (1140) releasably secure buttress assembly (160) to platform (1120). In the present example, cartridge (1100) lacks arms (252). In some other versions, retainers (1140) are provided as a supplement to arms (252). It should therefore be understood that retainers (1140) may be used in combination with other features such as arms (252).

Figure 24C:
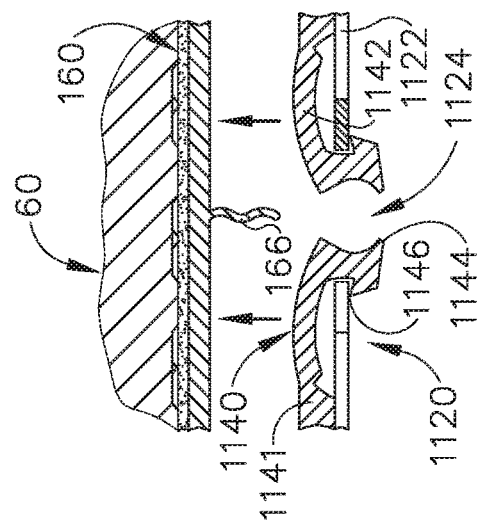
FIG. 24C depicts a partial, cross-sectional detail view of the anvil of the end effector of FIG. 2 with the buttress assembly adhered thereto, spaced away from the retention feature, with the retention feature remaining in the deflected state.
Figure 24B:
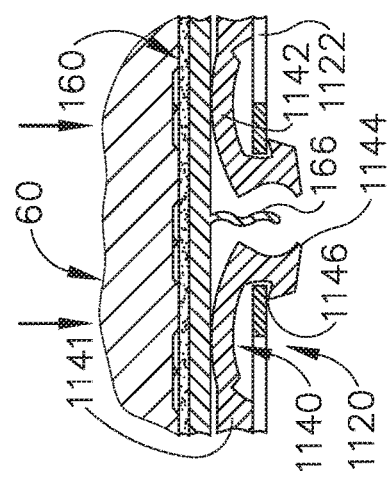
FIG. 24B depicts a partial, cross-sectional detail view of the anvil of the end effector of FIG. 2 compressing the buttress assembly against the retention feature, thereby deflecting the retention feature.
Figure 24A:
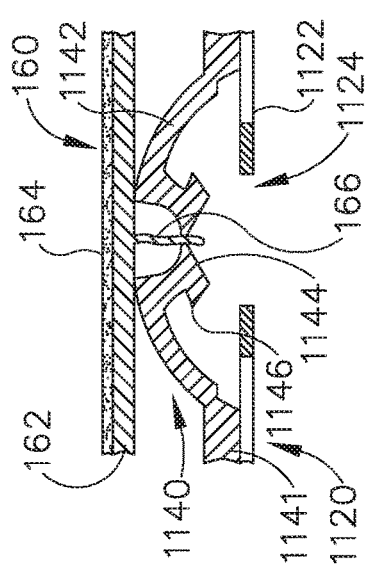
FIG. 24A depicts a partial, cross-sectional detail view of a retention feature of the buttress applier cartridge of FIG. 23, with the retention feature securing a buttress assembly to the buttress applier cartridge.

As best seen in FIGS. 24A-24C, buttress assembly (160) comprises a body (162) and an adhesive layer (164). Body (162) includes a plurality of integral filaments (166) extending downwardly therefrom. Each filament (166) is associated with a corresponding retainer (1140) as will be described in greater detail below. Aside from the inclusion of filaments (166), buttress assembly (160) may be configured and operable just like buttress assemblies (100, 110) described above.

As also best seen in FIGS. 24A-24C, platform (1120) of the present example comprises a rigid base (1122) that defines a plurality of openings (1124). Each opening (1124) is associated with a corresponding retainer (1140) as will be described in greater detail below.

Each retainer (1140) comprises an annular base (1141) and a set of arms (1142) that are pivotably coupled with annular base (1141) via respective living hinges. Each annular base (1141) is secured to rigid base (1112) of platform in coaxial alignment with corresponding openings (1124). Each arm (1142) includes a filament engaging feature (1144) and a latching feature (1146). While two arms (1142) may be seen in FIGS. 24A-24C, it should be understood that each retainer (1140) may include any suitable number of arms (1142). It should also be understood that arms (1142) may be equidistantly spaced from each other in an angular array about the vertical axis passing through the center of opening (1124) and the center of annular base (1141).

FIG. 24A shows retainer (1140) engaging buttress assembly (160) before cartridge (1100) is engaged by end effector (40). At this stage, filament (166) is captured by filament engaging features (1144) of arms (1142). Arms (1142) are resiliently biased to maintain this engagement, such that filament engaging features (1144) together clamp against filament (166). Retainers (1140) thus secure buttress assembly (160) to platform (1120).

FIG. 24B shows anvil (60) clamping buttress assembly (160) against platform (1120). The force applied by anvil (60) causes arms (1142) to deflect downwardly. During this movement, filament engaging features (1144) disengage filament (166), thereby releasing filament (166). Also during this movement, latching features (1146) engage base (1122). It should be understood that arms (1142) may deform during the transition from the state shown in FIG. 24A to the state shown in FIG. 24B in order to enable latching features (1146) to pass through opening (1124) to engage base (1122). At this stage, adhesive layer (164) has adhered buttress assembly (160) to anvil (60) and latching features (1146) have secured retainer (1140) in a collapsed configuration. With buttress assembly (160) adhered to anvil (160) and released from retainer (1140), buttress assembly (160) may be freely pulled away from platform (1120) as end effector (40) is opened as shown in FIG. 24C. Retainer (1140) remains in the collapsed configuration as buttress assembly (160) is pulled away from platform (1120).

When anvil (60) is driven downwardly against buttress assembly (160) and platform (1120) as shown in FIG. 24B, staple cartridge (70) may be simultaneously driven upwardly against platform (1120) or some other portion of cartridge (1110). Regardless of whether cartridge (1110) includes features enabling a similar buttress assembly (160) to be applied to deck (73) of staple cartridge (70), cartridge (1100) may include features that enable retainers (1140) to reach the collapsed configuration shown in FIG. 24B without interference from deck (73) of staple cartridge (70). Various suitable ways in which cartridge (1100) may prevent upward clamping forces exerted by staple cartridge (70) from interfering with the collapse of retainers (1140) during closure of end effector (40) will be apparent to those of ordinary skill in the art in view of the teachings herein.

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a housing defining a gap configured to receive a portion of an end effector of a surgical stapler; (b) a platform, wherein a portion of the platform is exposed in the gap defined by the housing; (c) a first buttress assembly positioned on the platform, wherein the buttress assembly is exposed in the gap defined by the housing; and (d) at least one retainer member configured to selectively retain the first buttress assembly against the platform, wherein the at least one retainer member is further configured to release the first buttress assembly from the platform in response to a clamping action of an end effector positioned in the gap defined by the housing.

Example 2

The apparatus of Example 1, wherein the housing defines a U shape.

Example 3

The apparatus of any one or more of Examples 1 through 2, wherein the platform is formed of a compressible material.

Example 4

The apparatus of any one or more of Examples 1 through 3, wherein the first buttress assembly comprises: (i) a body, and (ii) an adhesive layer.

Example 5

The apparatus of Example 4, wherein the adhesive layer is exposed in the gap defined by the housing.

Example 6

The apparatus of any one or more of Examples 1 through 5, further comprising a second buttress assembly, wherein the first buttress assembly is positioned on a first side of the platform, wherein the second buttress assembly is positioned on a second side of the platform.

Example 7

The apparatus of any one or more of Examples 1 through 6, wherein the first buttress assembly comprises: (i) a first longitudinally extending portion, and (ii) a second longitudinally extending portion, wherein the second longitudinally extending portion is laterally spaced apart from the first longitudinally extending portion.

Example 8

The apparatus of Example 7, wherein the second longitudinally extending portion is laterally spaced apart from the first longitudinally extending portion by a distance corresponding to a width of a gap defined by a channel formed in an end effector in a surgical stapler.

Example 9

The apparatus of any one or more of Examples 1 through 25, wherein the platform comprises a plurality of protrusions, wherein the protrusions are configured to provide localized concentration of pressure against the first buttress assembly in response to a clamping action of an end effector positioned in the gap defined by the housing.

Example 10

The apparatus of Example 9, wherein the protrusions comprise a plurality of pegs.

Example 11

The apparatus of Example 9, wherein the protrusions comprise a plurality of peaks.

Example 12

The apparatus of any one or more of Examples 1 through 8, wherein the platform comprises: (i) a first portion, wherein the first portion is configured to transition from a non-compressed state to a compressed state, wherein the first portion is configured to return to the non-compressed state after being compressed to the compressed state, and (ii) a second portion, wherein the first portion is configured to transition from a non-compressed state to a compressed state, wherein the first portion is configured to not return to the non-compressed state after being compressed to the compressed state, wherein the first buttress assembly is positioned over the first portion and the second portion.

Example 13

The apparatus of any one or more of Examples 1 through 25, wherein the platform comprises: (i) a first portion, wherein the first portion is configured to transition from a non-compressed state to a compressed state, wherein the first portion is configured to return to the non-compressed state at a first rate of return after being compressed to the compressed state, and (ii) a second portion, wherein the first portion is configured to transition from a non-compressed state to a compressed state, wherein the second portion is configured to return to the non-compressed state at a second rate of return after being compressed to the compressed state, wherein the second rate of return is slower than the first rate of return, wherein the first buttress assembly is positioned over the first portion and the second portion.

Example 14

The apparatus of Example 12 or Example 13, wherein the first portion comprises a resilient member, wherein the second portion comprises a compressible foam material.

Example 15

The apparatus of Example 14, wherein the first portion further comprises an array of resilient members disposed in the foam material.

Example 16

The apparatus of Example 12 or Example 13, wherein the first portion comprises a first foam material, wherein the second portion comprises a second foam material.

Example 17

The apparatus of Example 16, wherein the first portion further comprises an array of first foam material regions disposed in the second foam material.

Example 18

The apparatus of any one or more of Examples 1 through 17, wherein the platform further comprises: (i) a first region, wherein the first region has a first density, and (ii) a second region, wherein the second region has a second density, wherein the first density is greater than the second region, wherein the first buttress assembly is positioned over the first region and the second region.

Example 19

The apparatus of Example 18, wherein the platform further comprises a third region, wherein the third region has the first density, wherein the first buttress assembly is further positioned over the third region, wherein the second region is laterally interposed between the first and third regions.

Example 20

The apparatus of any one or more of Examples 1 through 17, wherein the platform further comprises: (i) a first region, wherein the first region has a first thickness, and (ii) a second region, wherein the second region has a second thickness, wherein the first thickness is greater than the second thickness, wherein the first buttress assembly is positioned over the first region and the second region.

Example 21

The apparatus of Example 20, wherein the platform further comprises a third region, wherein the third region has the first thickness, wherein the first buttress assembly is further positioned over the third region, wherein the second region is laterally interposed between the first and third regions.

Example 22

The apparatus of Example 20, wherein the platform has a first longitudinal end and a second longitudinal end, wherein the first region is located at the first longitudinal end and the second region is located at the second longitudinal end such that the first longitudinal end is thicker than the second longitudinal end.

Example 23

The apparatus of Example 22, wherein the platform defines a substantially smooth taper from the first longitudinal end to the second longitudinal end.

Example 24

The apparatus of Example 20, wherein the platform further comprises a third region, wherein the third region has the second thickness, wherein the first buttress assembly is further positioned over the third region, wherein the second region is longitudinally interposed between the first and third regions.

Example 25

The apparatus of Example 24, wherein the platform defines a curve to provide a substantially smooth transition from the first region to the second region and further to the third region.

Example 26

The apparatus of any one or more of Examples 1 through 25, wherein the at least one retainer member comprises: (i) a first head positioned on a first side of the platform, wherein the first head is configured to retain the first buttress assembly against the first side of the platform, (ii) a second head positioned on a second side of the platform, and (iii) an intermediate portion extending from the first head to the second head, wherein the intermediate portion passes through the platform.

Example 27

The apparatus of Example 44, wherein the intermediate portion is configured to compress from a first height to a second height in response to a clamping action of an end effector positioned in the gap defined by the housing.

Example 28

The apparatus of Example 27, wherein the intermediate portion comprises a first section and a second section, wherein the first section is configured to be pressed into the second section in response to a clamping action of an end effector positioned in the gap defined by the housing and thereby maintain the intermediate portion at the second height.

Example 29

The apparatus of Example 26, wherein the intermediate portion is frangible such that the first and second heads break free from the intermediate portion in response to the intermediate portion being compressed from the first height to the second height.

Example 30

The apparatus of any one or more of Examples 1 through 29, wherein the first buttress assembly comprises at least one thread extending toward the platform, wherein the at least one retainer member comprises a latching member configured to selectively grasp and release the at least one thread.

Example 31

The apparatus of Example 30, wherein the latching member is configured to transition from a non-collapsed configuration to a collapsed configuration in response to a clamping action of an end effector positioned in the gap defined by the housing, wherein the latching member is configured to grasp the at least one thread when the latching member is in the non-collapsed configuration, wherein the latching member is configured to release the at least one thread when latching member is in the collapsed configuration.

Example 32

The apparatus of Example 31, wherein the platform further comprises a base, wherein the latching member further comprises latching features that are configured to latchingly engage the base in response to the latching member transitioning to the collapsed configuration, such that the latching features are configured to cooperate with the base to hold the latching member in the collapsed configuration.

Example 33

An apparatus comprising: (a) a housing defining a gap configured to receive a portion of an end effector of a surgical stapler; (b) a platform, wherein a portion of the platform is exposed in the gap defined by the housing; and (c) a first buttress assembly positioned on the platform, wherein the buttress assembly is exposed in the gap defined by the housing; wherein the platform is configured to apply at least two different amounts of pressure against the first buttress assembly in response to a clamping action of an end effector positioned in the gap defined by the housing.

Example 34

The apparatus of Example 33, further comprising at least one retainer member configured to selectively retain the first buttress assembly against the platform, wherein the at least one retainer member is further configured to release the first buttress assembly from the platform in response to a clamping action of an end effector positioned in the gap defined by the housing

Example 35

An apparatus comprising: (a) a housing defining a gap configured to receive a portion of an end effector of a surgical stapler; (b) a platform, wherein a portion of the platform is exposed in the gap defined by the housing; and (c) a buttress assembly positioned on the platform, wherein the buttress assembly is exposed in the gap defined by the housing; wherein the platform comprises a plurality of protrusions, wherein the protrusions are configured to provide localized concentration of pressure against the first buttress assembly in response to a clamping action of an end effector positioned in the gap defined by the housing.

Example 36

A method of securing a buttress to an end effector, wherein the end effector comprises an upper jaw member and a lower jaw member, the method comprising: (a) positioning a platform of a buttress applier cartridge between the upper and lower jaw members while the upper and lower jaw members are in an open configuration, wherein the platform has a buttress disposed thereon during the act of positioning the platform between the upper and lower jaw members; (b) driving one or both of the upper or lower jaw members toward the platform to thereby engage the buttress with the end effector, wherein the platform applies localized pressure in a plurality of discrete locations on the buttress against the end effector in response to the act of driving one or both of the upper or lower jaw members toward the platform; and (c) driving one or both of the upper or lower jaw members way from the platform to thereby pull the buttress off of the platform.

VII. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein; U.S. patent application Ser. No. 14/827,856, entitled "Implantable Layers for a Surgical Instrument," filed Aug. 17, 2015, published as U.S. Pub. No. 2017/0049444 on Feb. 23, 2017, the disclosure of which is incorporated by reference herein; U.S. patent application Ser. No. 14/871,071, entitled "Compressible Adjunct with Crossing Spacer Fibers," filed Sep. 30, 2015, issued as U.S. Pat. No. 10,433,846 on Oct. 8, 2019, the disclosure of which is incorporated by reference herein; and U.S. patent application Ser. No. 14/871,131, entitled "Method for Applying an Implantable Layer to a Fastener Cartridge," filed Sep. 30, 2015, published as U.S. Pub. No. 2017/008642 on Mar. 30, 2017, the disclosure of which is incorporated by reference herein. Furthermore, in addition to the methods described herein, any of the various buttress assemblies described herein may be applied to end effector (40) in accordance with at least some of the teachings of U.S. Provisional Patent App. No. 62/209,041, entitled "Method and Apparatus for Applying a Buttress to End Effector of a Surgical Stapler," filed Aug. 24, 2015, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/

0199630, entitled "Robotically-Controlled Surgical Instruments," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,80,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
    (a) a housing defining a gap configured to receive a portion of an end effector of a surgical stapler;
    (b) a platform, wherein a portion of the platform is exposed in the gap defined by the housing;
    (c) a first buttress assembly supported by the platform, wherein the first buttress assembly is exposed in the gap defined by the housing, wherein the first buttress assembly includes at least one filament extending therefrom; and
    (d) at least one retainer configured to selectively retain the at least one filament of the first buttress assembly against the platform, wherein the at least one retainer is configured to release the at least one filament from the platform in response to a clamping action of the end effector positioned in the gap defined by the housing.
2. The apparatus of claim 1, further comprising:
    a second buttress assembly, wherein the first buttress assembly is positioned on a first side of the platform, wherein the second buttress assembly is positioned on a second side of the platform that is opposite the first side of the platform.
3. The apparatus of claim 1, wherein the first buttress assembly comprises: (i) a body, and (ii) an adhesive layer, wherein the adhesive layer is exposed in the gap defined by the housing.
4. The apparatus of claim 3, wherein the at least one filament comprises a plurality of filaments, wherein the plurality of filaments are integrally formed with the body of the first buttress assembly and extend from the body.
5. The apparatus of claim 4, wherein the at least one retainer comprises a plurality of retainers, wherein each filament of the plurality of the filaments is associated with a corresponding retainer of the plurality of retainers in a 1:1 relationship.
6. The apparatus of claim 1, wherein the platform comprises a rigid base that defines a plurality of openings, wherein each opening of the plurality of openings is associated with a corresponding retainer in a 1:1 relationship.
7. The apparatus of claim 1, wherein the at least one retainer comprises an annular base and a set of arms, wherein the arms are pivotably coupled with the annular base.
8. The apparatus of claim 7, wherein each annular base is coaxially secured to the platform, wherein the opening is disposed coaxially surrounded by the retainer.
9. The apparatus of claim 7, wherein the arms are equidistantly spaced from each other in an angular array about the vertical axis passing through a center of the opening and the center of the annular base.

10. The apparatus of claim 7, wherein each arm includes a filament engaging feature and a latching feature, wherein filament engaging feature is configured to engage the filament, wherein the latching feature is configured to engage the platform.

11. The apparatus of claim 10, wherein the at least one retainer is configured to engage the buttress assembly, such that the filament is captured by the filament engaging feature of the arms.

12. The apparatus of claim 10, wherein the arms of the at least one retainer are resiliently biased to maintain engagement with the filament, such that the filament engaging feature of the arms together clamp against the filament to secure the buttress assembly to the platform.

13. The apparatus of claim 10, wherein clamping of the buttress assembly against the platform is configured to cause the arms to deflect downwardly.

14. The apparatus of claim 10, wherein the filament engaging feature of the arms are configured to disengage the filament causing the filament to be released and the latching features are configured to be pushed downwards toward the platform to engage an underside of the platform.

15. The apparatus of claim 10, wherein the adhesive layer is configured adhere the buttress assembly to an anvil and the latching feature of the arms is configured to secure the retainer to the platform in a collapsed configuration, and wherein the retainer reaches the collapsed configuration without interference from a deck of a staple cartridge.

16. An apparatus comprising:
(a) a housing defining a gap configured to receive a portion of an end effector of a surgical stapler;
(b) a platform, wherein a portion of the platform is exposed in the gap defined by the housing;
(c) a first buttress assembly supported by the platform, wherein the first buttress assembly is exposed in the gap defined by the housing, wherein the first buttress assembly includes a plurality of downward projections extending therefrom and toward the platform; and
(d) a plurality of retainers configured to selectively retain the plurality of downward projections of the first buttress assembly against the platform, wherein the plurality of retainers are configured to release the first buttress assembly from the platform in response to a clamping action of the end effector positioned in the gap defined by the housing.

17. The apparatus of claim 16, wherein each downward projection includes a filament that is integrally formed with the first buttress assembly, wherein each retainer of the plurality of retainers includes a base and a set of arms, wherein each arm includes a filament engaging feature configured to engage the filament and a latching feature configured to engage the platform.

18. The apparatus of claim 17, wherein each of the filament engaging feature of the arms is configured to disengage the filament causing the filament to be released and the latching features are configured to be pushed downwards toward the platform to engage an underside of the platform.

19. An apparatus comprising:
(a) a housing defining a gap configured to receive a portion of an end effector of a surgical stapler;
(b) a platform, wherein a portion of the platform is exposed in the gap defined by the housing;
(c) a first buttress assembly positioned on supported by the platform, wherein the first buttress assembly is exposed in the gap defined by the housing, wherein the first buttress assembly comprises:
(i) a body includes a plurality of filaments that are integrally formed with the first buttress assembly and extend from the first buttress assembly towards the platform, and
(ii) an adhesive layer, wherein the adhesive layer is exposed in the gap defined by the housing; and
(d) a plurality of retainers configured to selectively retain the first buttress assembly against the platform, wherein the plurality of retainers are further configured to release the first buttress assembly from the platform in response to a clamping action of the end effector positioned in the gap defined by the housing, wherein each retainer comprises:
(i) a base secured to the platform, and
(ii) at least two arms, wherein each arm includes:
(A) a filament engaging feature configured to releasable hold the filament, wherein the filament engaging feature is configured to disengage the filament causing the filament to be released, and
(B) a latching feature configured to contact an underside of the platform, wherein the latching feature is configured to be pushed towards the platform and engage an underside of the platform.

20. The apparatus of claim 19, wherein the first buttress assembly is configured to be freely pulled away from the platform as the end effector is opened, and wherein the plurality of retainers are configured to remain in a collapsed configuration as the first buttress assembly is pulled away from the platform.

\* \* \* \* \*